(12) United States Patent
Estes

(10) Patent No.: US 11,464,906 B2
(45) Date of Patent: *Oct. 11, 2022

(54) INFUSION PUMP SYSTEM AND METHOD

(71) Applicant: Bigfoot Biomedical, Inc., Milpitas, CA (US)

(72) Inventor: Mark C. Estes, Malibu, CA (US)

(73) Assignee: Bigfoot Biomedical, Inc., Milpitas, CA (US)

(*) Notice: Subject to any disclaimer, the term of this patent is extended or adjusted under 35 U.S.C. 154(b) by 236 days.

This patent is subject to a terminal disclaimer.

(21) Appl. No.: 16/743,332

(22) Filed: Jan. 15, 2020

(65) Prior Publication Data
US 2020/0147305 A1 May 14, 2020

Related U.S. Application Data

(63) Continuation of application No. 14/094,185, filed on Dec. 2, 2013, now Pat. No. 10,569,015.

(51) Int. Cl.
*A61M 5/172* (2006.01)
*A61M 5/142* (2006.01)

(52) U.S. Cl.
CPC ........ *A61M 5/172* (2013.01); *A61M 5/14244* (2013.01); *A61M 2005/14208* (2013.01); *A61M 2205/3569* (2013.01); *A61M 2205/3576* (2013.01); *A61M 2205/502* (2013.01); *A61M 2205/80* (2013.01)

(58) Field of Classification Search
CPC .. A61M 5/142; A61M 5/172; A61M 5/14244; A61M 2205/80; A61M 2205/502; A61M 2205/3569; A61M 2205/3576; A61M 2005/14208
See application file for complete search history.

(56) References Cited

U.S. PATENT DOCUMENTS

| 2,605,765 | A | 8/1952 | Kollsman |
| 3,688,764 | A | 9/1972 | Owen |
| 3,886,938 | A | 6/1975 | Szabo et al. |
| 4,077,405 | A | 3/1978 | Haerten et al. |
| 4,151,845 | A | 5/1979 | Clemens |

(Continued)

FOREIGN PATENT DOCUMENTS

| CA | 2543545 | 5/2005 |
| DE | 19627619 | 1/1998 |

(Continued)

OTHER PUBLICATIONS

Accu-Chek Spirit, "Pump Therapy Made for You," Roche, 2006, 6 pages.

(Continued)

*Primary Examiner* — Nilay J Shah
(74) *Attorney, Agent, or Firm* — TraskBritt

(57) ABSTRACT

Some embodiments of an infusion pump system may be configured to allow the user to communicate with the infusion pump system using voice or image input. Optionally, particular embodiments can interpret the voice or image input using speech or image recognition capabilities. By incorporating speech or image recognition equipment within the infusion pump system, user interactions with the pump system can be enhanced and simplified.

20 Claims, 5 Drawing Sheets

(56) References Cited

U.S. PATENT DOCUMENTS

| | | |
|---|---|---|
| 4,231,368 A | 11/1980 | Becker |
| 4,235,234 A | 11/1980 | Martin et al. |
| 4,265,241 A | 5/1981 | Portner et al. |
| 4,300,554 A | 11/1981 | Hessberg et al. |
| 4,313,439 A | 2/1982 | Babb et al. |
| 4,373,527 A | 2/1983 | Fischell |
| 4,398,908 A | 8/1983 | Siposs |
| 4,435,173 A | 3/1984 | Siposs et al. |
| 4,443,218 A | 4/1984 | Decant et al. |
| 4,475,901 A | 10/1984 | Kraegen et al. |
| 4,493,704 A | 1/1985 | Beard et al. |
| 4,529,401 A | 7/1985 | Leslie et al. |
| 4,552,561 A | 11/1985 | Eckenhoff et al. |
| 4,564,054 A | 1/1986 | Gustavsson |
| 4,652,260 A | 3/1987 | Fenton et al. |
| 4,668,220 A | 5/1987 | Hawrylenko |
| 4,681,569 A | 7/1987 | Coble et al. |
| 4,731,726 A | 3/1988 | Allen, III |
| 4,734,092 A | 3/1988 | Millerd |
| 4,749,109 A | 6/1988 | Kamen |
| 4,768,506 A | 9/1988 | Parker et al. |
| 4,838,857 A | 6/1989 | Strowe et al. |
| 4,850,817 A | 7/1989 | Nason et al. |
| 4,902,278 A | 2/1990 | Maget et al. |
| 5,029,591 A | 7/1991 | Teves |
| 5,045,064 A | 9/1991 | Idriss |
| 5,088,981 A | 2/1992 | Howson et al. |
| 5,088,990 A | 2/1992 | Hivale et al. |
| 5,176,632 A | 1/1993 | Bernardi |
| 5,190,522 A | 3/1993 | Wojcicki et al. |
| 5,209,230 A | 5/1993 | Swedlow et al. |
| 5,225,763 A | 7/1993 | Krohn et al. |
| 5,250,027 A | 10/1993 | Lewis et al. |
| 5,261,882 A | 11/1993 | Sealfon |
| 5,314,412 A | 5/1994 | Rex |
| 5,335,994 A | 8/1994 | Weynant nee Girones |
| 5,338,157 A | 8/1994 | Blomquist |
| 5,342,180 A | 8/1994 | Daoud |
| 5,349,575 A | 9/1994 | Park |
| 5,389,078 A | 2/1995 | Zalesky et al. |
| 5,395,340 A | 3/1995 | Lee |
| 5,411,487 A | 5/1995 | Castagna |
| 5,545,143 A | 8/1996 | Fischell et al. |
| 5,551,850 A | 9/1996 | Williamson et al. |
| 5,554,123 A | 9/1996 | Herskowitz |
| 5,569,186 A | 10/1996 | Lord et al. |
| 5,626,566 A | 5/1997 | Petersen et al. |
| 5,637,095 A | 6/1997 | Nason et al. |
| 5,656,032 A | 8/1997 | Kriesel et al. |
| 5,665,065 A | 9/1997 | Colman et al. |
| 5,672,167 A | 9/1997 | Athayde et al. |
| 5,693,018 A | 12/1997 | Kriesel et al. |
| 5,718,562 A | 2/1998 | Lawless |
| 5,741,216 A | 4/1998 | Hemmingsen et al. |
| 5,766,155 A | 6/1998 | Hyman et al. |
| 5,772,635 A | 6/1998 | Dastur et al. |
| 5,800,420 A | 9/1998 | Grose et al. |
| 5,816,306 A | 10/1998 | Giacomel |
| 5,822,715 A | 10/1998 | Worthington et al. |
| 5,851,197 A | 12/1998 | Marano et al. |
| 5,852,803 A | 12/1998 | Ashby et al. |
| 5,858,001 A | 1/1999 | Tsals et al. |
| 5,858,005 A | 1/1999 | Kriesel |
| 5,873,731 A | 2/1999 | Prendergast |
| 5,893,838 A | 4/1999 | Daoud et al. |
| 5,914,941 A | 6/1999 | Janky |
| 5,919,167 A | 7/1999 | Mulhauser et al. |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,056,728 A | 5/2000 | Von Schuckmann |
| 6,074,372 A | 6/2000 | Hansen |
| 6,106,498 A | 8/2000 | Friedli |
| 6,110,149 A | 8/2000 | Klitgaard et al. |
| 6,126,595 A | 10/2000 | Amano et al. |
| 6,127,061 A | 10/2000 | Shun et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,233,471 B1 | 5/2001 | Berner et al. |
| 6,248,067 B1 | 6/2001 | Causey, III et al. |
| 6,248,090 B1 | 6/2001 | Jensen et al. |
| 6,248,093 B1 | 6/2001 | Moberg |
| 6,251,113 B1 | 6/2001 | Appelbaum et al. |
| 6,269,340 B1 | 7/2001 | Ford et al. |
| 6,277,098 B1 | 8/2001 | Klitmose et al. |
| 6,292,440 B1 | 9/2001 | Lee |
| 6,302,855 B1 | 10/2001 | Lav et al. |
| 6,302,869 B1 | 10/2001 | Klitgaard |
| 6,368,314 B1 | 4/2002 | Kipfer et al. |
| 6,375,638 B2 | 4/2002 | Nason et al. |
| 6,379,301 B1 | 4/2002 | Worthington et al. |
| 6,379,339 B1 | 4/2002 | Klitgaard et al. |
| 6,381,496 B1 | 4/2002 | Meadows et al. |
| 6,397,098 B1 | 5/2002 | Uber et al. |
| 6,404,098 B1 | 6/2002 | Kayama et al. |
| 6,427,088 B1 | 7/2002 | Bowman, IV et al. |
| D461,241 S | 8/2002 | Moberg et al. |
| D461,891 S | 8/2002 | Moberg |
| 6,434,528 B1 | 8/2002 | Sanders |
| 6,436,072 B1 | 8/2002 | Kullas et al. |
| 6,461,329 B1 | 10/2002 | Van et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,491,684 B1 | 12/2002 | Joshi et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,537,268 B1 | 3/2003 | Gibson et al. |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,345 B1 | 5/2003 | Houben et al. |
| 6,558,351 B1 | 5/2003 | Steil et al. |
| 6,562,001 B2 | 5/2003 | Lebel et al. |
| 6,562,011 B1 | 5/2003 | Buch-Rasmussen |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,572,542 B1 | 6/2003 | Houben et al. |
| 6,572,545 B2 | 6/2003 | Knobbe et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,587,199 B1 | 7/2003 | Luu |
| 6,589,229 B1 | 7/2003 | Connelly et al. |
| 6,599,281 B1 | 7/2003 | Struys et al. |
| 6,605,067 B1 | 8/2003 | Larsen |
| 6,605,072 B2 | 8/2003 | Struys et al. |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |

(56) References Cited

U.S. PATENT DOCUMENTS

| | | |
|---|---|---|
| 6,663,602 B2 | 12/2003 | Møller |
| 6,668,196 B1 | 12/2003 | Villegas et al. |
| 6,669,668 B1 | 12/2003 | Kleeman et al. |
| 6,669,669 B2 | 12/2003 | Flaherty et al. |
| 6,685,674 B2 | 2/2004 | Douglas et al. |
| 6,687,546 B2 | 2/2004 | Lebel et al. |
| 6,689,100 B2 | 2/2004 | Connelly et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,723,077 B2 | 4/2004 | Pickup et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,785 B2 | 6/2004 | Van et al. |
| 6,752,787 B1 | 6/2004 | Causey, III et al. |
| 6,758,810 B2 | 7/2004 | Lebel et al. |
| 6,761,286 B2 | 7/2004 | Py et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,957 B2 | 9/2004 | Carpenter et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B2 | 7/2005 | Whitehurst |
| 6,923,763 B1 | 8/2005 | Kovatchev et al. |
| 6,925,393 B1 | 8/2005 | Kalatz et al. |
| 6,936,006 B2 | 8/2005 | Sabra |
| 6,936,029 B2 | 8/2005 | Maim et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,060,059 B2 | 6/2006 | Keith et al. |
| 7,066,910 B2 | 6/2006 | Bauhahn et al. |
| 7,070,580 B2 | 7/2006 | Nielsen |
| 7,098,803 B2 | 8/2006 | Mann et al. |
| 7,104,972 B2 | 9/2006 | Møller et al. |
| 7,109,878 B2 | 9/2006 | Mann et al. |
| 7,123,964 B2 | 10/2006 | Betzold et al. |
| 7,128,727 B2 | 10/2006 | Flaherty et al. |
| 7,133,329 B2 | 11/2006 | Skyggebjerg et al. |
| 7,172,572 B2 | 2/2007 | Diamond et al. |
| 7,179,226 B2 | 2/2007 | Crothall et al. |
| 7,204,823 B2 | 4/2007 | Estes et al. |
| 7,220,240 B2 | 5/2007 | Struys et al. |
| 7,232,423 B2 | 6/2007 | Mernoe |
| 7,267,665 B2 | 9/2007 | Steil et al. |
| 7,291,107 B2 | 11/2007 | Hellwig et al. |
| 7,354,420 B2 | 4/2008 | Steil et al. |
| 7,402,153 B2 | 7/2008 | Steil et al. |
| 7,404,796 B2 | 7/2008 | Ginsberg |
| 7,429,255 B2 | 9/2008 | Thompson |
| 7,491,187 B2 | 2/2009 | Van et al. |
| 7,494,481 B2 | 2/2009 | Moberg et al. |
| 7,547,281 B2 | 6/2009 | Hayes et al. |
| 7,553,281 B2 | 6/2009 | Hellwig |
| 7,569,030 B2 | 8/2009 | Lebel et al. |
| 7,569,050 B2 | 8/2009 | Moberg et al. |
| 7,570,980 B2 | 8/2009 | Ginsberg |
| 7,591,801 B2 | 9/2009 | Brauker et al. |
| 7,597,682 B2 | 10/2009 | Moberg |
| 7,641,649 B2 | 1/2010 | Moberg et al. |
| 7,651,845 B2 | 1/2010 | Doyle et al. |
| 7,654,982 B2 | 2/2010 | Carlisle et al. |
| 7,670,288 B2 | 3/2010 | Sher |
| 7,708,717 B2 | 5/2010 | Estes et al. |
| 7,734,323 B2 | 6/2010 | Blomquist et al. |
| 7,785,313 B2 | 8/2010 | Mastrototaro |
| 7,789,859 B2 | 9/2010 | Estes et al. |
| 7,794,426 B2 | 9/2010 | Briones et al. |
| 7,806,853 B2 | 10/2010 | Wittmann et al. |
| 7,806,854 B2 | 10/2010 | Damiano et al. |
| 7,815,602 B2 | 10/2010 | Mann et al. |
| 7,819,843 B2 | 10/2010 | Mann et al. |
| 7,828,528 B2 | 11/2010 | Estes et al. |
| 7,850,641 B2 | 12/2010 | Lebel et al. |
| 7,875,022 B2 | 1/2011 | Wenger et al. |
| 7,904,061 B1 | 3/2011 | Zaffino et al. |
| 7,938,797 B2 | 5/2011 | Estes |
| 7,938,801 B2 | 5/2011 | Hawkins et al. |
| 7,946,985 B2 | 5/2011 | Mastrototaro et al. |
| 7,959,598 B2 | 6/2011 | Estes |
| 7,967,812 B2 | 6/2011 | Jasperson et al. |
| 7,976,492 B2 | 7/2011 | Brauker et al. |
| 8,029,459 B2 | 10/2011 | Rush et al. |
| 8,062,249 B2 | 11/2011 | Wilinska et al. |
| 8,105,268 B2 | 1/2012 | Lebel et al. |
| 8,114,023 B2 | 2/2012 | Ward et al. |
| 8,152,789 B2 | 4/2012 | Starkweather et al. |
| 8,206,296 B2 | 6/2012 | Jennewine |
| 8,206,350 B2 | 6/2012 | Mann et al. |
| 8,208,984 B2 | 6/2012 | Blomquist et al. |
| 8,221,385 B2 | 7/2012 | Estes |
| 8,226,556 B2 | 7/2012 | Hayes et al. |
| 8,246,540 B2 | 8/2012 | Ginsberg |
| 8,262,616 B2 | 9/2012 | Grant et al. |
| 8,267,893 B2 | 9/2012 | Moberg et al. |
| 8,273,052 B2 | 9/2012 | Damiano et al. |
| D669,165 S | 10/2012 | Sims et al. |
| 8,282,626 B2 | 10/2012 | Wenger et al. |
| 8,287,487 B2 | 10/2012 | Estes |
| 8,318,154 B2 | 11/2012 | Frost et al. |
| 8,348,844 B2 | 1/2013 | Kunjan et al. |
| 8,348,886 B2 | 1/2013 | Kanderian et al. |
| 8,348,923 B2 | 1/2013 | Kanderian et al. |
| 8,352,011 B2 | 1/2013 | Van et al. |
| 8,372,039 B2 | 2/2013 | Mernoe et al. |
| 8,417,311 B2 | 4/2013 | Rule |
| 8,430,847 B2 | 4/2013 | Mernoe et al. |
| 8,439,834 B2 | 5/2013 | Schmelzeisen-Redeker et al. |
| 8,439,897 B2 | 5/2013 | Yodfat et al. |
| 8,454,576 B2 | 6/2013 | Mastrototaro et al. |
| 8,460,231 B2 | 6/2013 | Brauker et al. |
| 8,467,972 B2 | 6/2013 | Rush |

(56) References Cited

U.S. PATENT DOCUMENTS

| | | |
|---|---|---|
| 8,475,409 B2 | 7/2013 | Tsoukalis |
| 8,480,655 B2 | 7/2013 | Jasperson et al. |
| 8,548,544 B2 | 10/2013 | Kircher et al. |
| 8,548,552 B2 | 10/2013 | Tsoukalis |
| 8,551,045 B2 | 10/2013 | Sie et al. |
| 8,560,082 B2 | 10/2013 | Wei |
| 8,560,131 B2 | 10/2013 | Haueter et al. |
| 8,562,558 B2 | 10/2013 | Kamath et al. |
| 8,562,587 B2 | 10/2013 | Kovatchev et al. |
| 8,568,713 B2 | 10/2013 | Frost et al. |
| 8,579,854 B2 | 11/2013 | Budiman et al. |
| 8,579,879 B2 | 11/2013 | Palerm et al. |
| 8,585,591 B2 | 11/2013 | Sloan et al. |
| 8,585,593 B2 | 11/2013 | Kovatchev et al. |
| 8,585,637 B2 | 11/2013 | Wilinska et al. |
| 8,585,638 B2 | 11/2013 | Blomquist |
| 8,597,274 B2 | 12/2013 | Sloan et al. |
| 8,615,366 B2 | 12/2013 | Galley et al. |
| 8,622,988 B2 | 1/2014 | Hayter |
| 8,679,016 B2 | 3/2014 | Mastrototaro et al. |
| 8,679,060 B2 | 3/2014 | Mernoe et al. |
| 8,690,820 B2 | 4/2014 | Cinar et al. |
| 8,694,115 B2 | 4/2014 | Goetz et al. |
| 8,706,691 B2 | 4/2014 | Mcdaniel et al. |
| 8,718,949 B2 | 5/2014 | Blomquist et al. |
| 8,721,585 B2 | 5/2014 | Brauker et al. |
| 8,727,982 B2 | 5/2014 | Jennewine |
| 8,734,422 B2 | 5/2014 | Hayter |
| 8,734,428 B2 | 5/2014 | Blomquist |
| 8,747,315 B2 | 6/2014 | Brauker et al. |
| 8,762,070 B2 | 6/2014 | Doyle et al. |
| 8,771,222 B2 | 7/2014 | Kanderian et al. |
| 8,777,896 B2 | 7/2014 | Starkweather et al. |
| 8,777,924 B2 | 7/2014 | Kanderian et al. |
| 8,784,364 B2 | 7/2014 | Kamen et al. |
| 8,784,369 B2 | 7/2014 | Starkweather et al. |
| 8,784,370 B2 | 7/2014 | Lebel et al. |
| 8,795,224 B2 | 8/2014 | Starkweather et al. |
| 8,795,252 B2 | 8/2014 | Hayter |
| 8,808,230 B2 | 8/2014 | Rotstein |
| 8,876,755 B2 | 11/2014 | Taub et al. |
| 8,882,741 B2 | 11/2014 | Brauker et al. |
| 8,903,501 B2 | 12/2014 | Perryman |
| 8,919,180 B2 | 12/2014 | Gottlieb et al. |
| 8,920,401 B2 | 12/2014 | Brauker et al. |
| 8,926,585 B2 | 1/2015 | Brauker et al. |
| 8,945,094 B2 | 2/2015 | Nordh |
| 8,956,291 B2 | 2/2015 | Valk et al. |
| 8,956,321 B2 | 2/2015 | Dejournett |
| 8,977,504 B2 | 3/2015 | Hovorka |
| 8,992,475 B2 | 3/2015 | Mann et al. |
| 9,034,323 B2 | 5/2015 | Frost et al. |
| 9,050,413 B2 | 6/2015 | Brauker et al. |
| 9,056,165 B2 | 6/2015 | Steil et al. |
| 9,056,168 B2 | 6/2015 | Kircher et al. |
| 9,078,963 B2 | 7/2015 | Estes |
| 9,089,305 B2 | 7/2015 | Hovorka |
| 9,149,233 B2 | 10/2015 | Kamath et al. |
| 9,155,843 B2 | 10/2015 | Brauker et al. |
| 9,247,901 B2 | 2/2016 | Kamath et al. |
| 9,314,566 B2 | 4/2016 | Wenger et al. |
| 9,320,471 B2 | 4/2016 | Hayes et al. |
| 9,333,298 B2 | 5/2016 | Kim et al. |
| 9,415,157 B2 | 8/2016 | Mann et al. |
| 9,474,855 B2 | 10/2016 | Mccann et al. |
| 9,480,796 B2 | 11/2016 | Starkweather et al. |
| 9,486,172 B2 | 11/2016 | Cobelli et al. |
| 9,486,578 B2 | 11/2016 | Finan et al. |
| 9,561,324 B2 | 2/2017 | Estes |
| 9,878,097 B2 | 1/2018 | Estes |
| 9,968,729 B2 | 5/2018 | Estes |
| 10,449,294 B1 | 10/2019 | Estes |
| 10,569,015 B2 | 2/2020 | Estes |
| 2001/0003542 A1 | 6/2001 | Kita |
| 2001/0041869 A1 | 11/2001 | Causey, III et al. |
| 2001/0056262 A1 | 12/2001 | Cabiri |
| 2002/0002326 A1 | 1/2002 | Causey, III et al. |
| 2002/0004651 A1 | 1/2002 | Ljndggreen et al. |
| 2002/0007154 A1 | 1/2002 | Hansen et al. |
| 2002/0013784 A1 | 1/2002 | Swanson |
| 2002/0016534 A1 | 2/2002 | Trepagnier et al. |
| 2002/0016568 A1 | 2/2002 | Lebel |
| 2002/0032402 A1 | 3/2002 | Daoud et al. |
| 2002/0040208 A1 | 4/2002 | Flaherty et al. |
| 2002/0046315 A1 | 4/2002 | Miller et al. |
| 2002/0055845 A1 | 5/2002 | Ueda et al. |
| 2002/0072720 A1 | 6/2002 | Hague et al. |
| 2002/0091358 A1 | 7/2002 | Klitmose |
| 2002/0107476 A1* | 8/2002 | Mann ............... A61M 5/1723 604/67 |
| 2002/0126036 A1 | 9/2002 | Flaherty et al. |
| 2002/0156462 A1 | 10/2002 | Stultz |
| 2002/0164973 A1 | 11/2002 | Janik et al. |
| 2003/0028089 A1 | 2/2003 | Galley |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0104982 A1 | 6/2003 | Wittmann et al. |
| 2003/0121055 A1 | 6/2003 | Kaminski et al. |
| 2003/0125672 A1 | 7/2003 | Adair et al. |
| 2003/0161744 A1 | 8/2003 | Vilks et al. |
| 2003/0198558 A1 | 10/2003 | Nason et al. |
| 2003/0199825 A1 | 10/2003 | Flaherty |
| 2003/0208113 A1 | 11/2003 | Mault et al. |
| 2003/0216683 A1 | 11/2003 | Shekalim |
| 2003/0216686 A1 | 11/2003 | Lynch et al. |
| 2004/0006316 A1 | 1/2004 | Patton |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0068230 A1 | 4/2004 | Estes et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0115068 A1 | 6/2004 | Hansen et al. |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0158207 A1 | 8/2004 | Hunn et al. |
| 2004/0167464 A1 | 8/2004 | Ireland et al. |
| 2004/0171983 A1 | 9/2004 | Sparks et al. |
| 2004/0176720 A1 | 9/2004 | Kipfer |
| 2004/0176727 A1 | 9/2004 | Shekalim |
| 2004/0187952 A1 | 9/2004 | Jones |
| 2004/0204673 A1 | 10/2004 | Flaherty |
| 2004/0204744 A1 | 10/2004 | Penner et al. |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0010165 A1 | 1/2005 | Hickle |
| 2005/0021005 A1 | 1/2005 | Flaherty et al. |
| 2005/0021104 A1 | 1/2005 | DiLorenzo |
| 2005/0022274 A1 | 1/2005 | Campbell et al. |
| 2005/0033223 A1 | 2/2005 | Herrera |
| 2005/0038332 A1 | 2/2005 | Saidara et al. |
| 2005/0049179 A1 | 3/2005 | Davidson et al. |
| 2005/0065760 A1 | 3/2005 | Murtfeldt et al. |
| 2005/0090808 A1 | 4/2005 | Malave et al. |
| 2005/0090851 A1 | 4/2005 | Devlin |
| 2005/0095063 A1 | 5/2005 | Fathallah |
| 2005/0101933 A1 | 5/2005 | Marrs et al. |
| 2005/0107743 A1 | 5/2005 | Fangrow, Jr. |
| 2005/0113745 A1 | 5/2005 | Stultz |
| 2005/0124866 A1 | 6/2005 | Elaz et al. |
| 2005/0137530 A1 | 6/2005 | Campbell et al. |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |

(56) References Cited

U.S. PATENT DOCUMENTS

| | | |
|---|---|---|
| 2005/0234404 A1 | 10/2005 | Vilks et al. |
| 2005/0238507 A1 | 10/2005 | DiIanni et al. |
| 2005/0240544 A1 | 10/2005 | Kil et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2005/0277890 A1 | 12/2005 | Stewart et al. |
| 2006/0036214 A1 | 2/2006 | Mogensen et al. |
| 2006/0041229 A1 | 2/2006 | Garibotto et al. |
| 2006/0042633 A1 | 3/2006 | Bishop et al. |
| 2006/0069351 A9 | 3/2006 | Safabash et al. |
| 2006/0069382 A1 | 3/2006 | Pedersen |
| 2006/0074381 A1 | 4/2006 | Malave et al. |
| 2006/0075269 A1 | 4/2006 | Liong et al. |
| 2006/0095014 A1 | 5/2006 | Ethelfeld |
| 2006/0125654 A1 | 6/2006 | Liao et al. |
| 2006/0135913 A1 | 6/2006 | Ethelfeld |
| 2006/0142698 A1 | 6/2006 | Ethelfeld |
| 2006/0151545 A1 | 7/2006 | Imhof et al. |
| 2006/0173406 A1* | 8/2006 | Hayes ............... A61B 5/14532 604/67 |
| 2006/0173410 A1 | 8/2006 | Moberg et al. |
| 2006/0178633 A1 | 8/2006 | Garibotto et al. |
| 2006/0184104 A1 | 8/2006 | Cheney et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0214511 A1 | 9/2006 | Dayan |
| 2006/0247574 A1 | 11/2006 | Maule et al. |
| 2006/0247581 A1 | 11/2006 | Pedersen et al. |
| 2006/0253086 A1 | 11/2006 | Moberg et al. |
| 2006/0258973 A1 | 11/2006 | Volt |
| 2006/0258976 A1 | 11/2006 | Shturman et al. |
| 2006/0264835 A1 | 11/2006 | Nielsen et al. |
| 2006/0264890 A1 | 11/2006 | Moberg et al. |
| 2006/0264894 A1 | 11/2006 | Moberg et al. |
| 2007/0016127 A1 | 1/2007 | Staib et al. |
| 2007/0060870 A1 | 3/2007 | Tolle et al. |
| 2007/0073228 A1 | 3/2007 | Mernoe et al. |
| 2007/0073235 A1 | 3/2007 | Estes |
| 2007/0073236 A1 | 3/2007 | Mernoe et al. |
| 2007/0078818 A1 | 4/2007 | Zivitz et al. |
| 2007/0079836 A1 | 4/2007 | Reghabi et al. |
| 2007/0088271 A1 | 4/2007 | Richards |
| 2007/0093750 A1 | 4/2007 | Jan et al. |
| 2007/0093786 A1 | 4/2007 | Goldsmith et al. |
| 2007/0100222 A1 | 5/2007 | Mastrototaro et al. |
| 2007/0106218 A1 | 5/2007 | Yodfat et al. |
| 2007/0112298 A1 | 5/2007 | Mueller et al. |
| 2007/0118364 A1* | 5/2007 | Wise ............... G10L 25/78 704/215 |
| 2007/0118405 A1 | 5/2007 | Campbell et al. |
| 2007/0123819 A1 | 5/2007 | Mernoe et al. |
| 2007/0124002 A1 | 5/2007 | Estes et al. |
| 2007/0142776 A9 | 6/2007 | Kovelman et al. |
| 2007/0155307 A1 | 7/2007 | Ng et al. |
| 2007/0156092 A1 | 7/2007 | Estes et al. |
| 2007/0156094 A1 | 7/2007 | Safabash et al. |
| 2007/0166170 A1 | 7/2007 | Nason et al. |
| 2007/0167905 A1 | 7/2007 | Estes et al. |
| 2007/0167912 A1 | 7/2007 | Causey et al. |
| 2007/0169607 A1 | 7/2007 | Keller et al. |
| 2007/0173761 A1 | 7/2007 | Kanderian et al. |
| 2007/0179444 A1 | 8/2007 | Causey et al. |
| 2007/0191702 A1 | 8/2007 | Yodfat et al. |
| 2007/0219432 A1 | 9/2007 | Thompson |
| 2007/0219480 A1 | 9/2007 | Kamen et al. |
| 2007/0233521 A1 | 10/2007 | Wehba et al. |
| 2007/0239116 A1 | 10/2007 | Follman et al. |
| 2007/0248238 A1 | 10/2007 | Abreu |
| 2007/0252774 A1 | 11/2007 | Qi et al. |
| 2007/0255250 A1 | 11/2007 | Moberg et al. |
| 2007/0282299 A1 | 12/2007 | Hellwig |
| 2007/0287931 A1 | 12/2007 | Dilorenzo |
| 2008/0009824 A1 | 1/2008 | Moberg et al. |
| 2008/0015422 A1 | 1/2008 | Wessel |
| 2008/0027574 A1 | 1/2008 | Thomas |
| 2008/0031481 A1 | 2/2008 | Warren et al. |
| 2008/0045891 A1 | 2/2008 | Maule et al. |
| 2008/0051697 A1 | 2/2008 | Mounce et al. |
| 2008/0051698 A1 | 2/2008 | Mounce et al. |
| 2008/0051714 A1 | 2/2008 | Moberg et al. |
| 2008/0051716 A1 | 2/2008 | Stutz |
| 2008/0051730 A1 | 2/2008 | Bikovsky |
| 2008/0051738 A1 | 2/2008 | Griffin |
| 2008/0077081 A1 | 3/2008 | Mounce et al. |
| 2008/0097326 A1 | 4/2008 | Moberg et al. |
| 2008/0097375 A1 | 4/2008 | Bikovsky |
| 2008/0097381 A1 | 4/2008 | Moberg et al. |
| 2008/0103022 A1 | 5/2008 | Dvorak et al. |
| 2008/0109050 A1 | 5/2008 | John |
| 2008/0125700 A1 | 5/2008 | Moberg et al. |
| 2008/0125701 A1 | 5/2008 | Moberg et al. |
| 2008/0129535 A1 | 6/2008 | Thompson et al. |
| 2008/0172027 A1 | 7/2008 | Blomquist |
| 2008/0177149 A1* | 7/2008 | Weinert ............... G16H 40/63 600/300 |
| 2008/0183060 A1 | 7/2008 | Steil et al. |
| 2008/0188796 A1 | 8/2008 | Steil et al. |
| 2008/0198012 A1* | 8/2008 | Kamen ............... G16H 40/67 340/572.1 |
| 2008/0201325 A1 | 8/2008 | Doniger et al. |
| 2008/0208627 A1 | 8/2008 | Skyggebjerg |
| 2008/0215035 A1 | 9/2008 | Yodfat et al. |
| 2008/0234630 A1 | 9/2008 | Iddan et al. |
| 2008/0255516 A1 | 10/2008 | Yodfat et al. |
| 2008/0269683 A1 | 10/2008 | Bikovsky |
| 2008/0269687 A1 | 10/2008 | Chong et al. |
| 2008/0269714 A1 | 10/2008 | Mastrototaro et al. |
| 2008/0269723 A1 | 10/2008 | Mastrototaro et al. |
| 2008/0294094 A1 | 11/2008 | Mhatre et al. |
| 2008/0294109 A1 | 11/2008 | Estes et al. |
| 2008/0294142 A1 | 11/2008 | Patel et al. |
| 2008/0300572 A1 | 12/2008 | Rankers et al. |
| 2008/0306434 A1 | 12/2008 | Dobbles et al. |
| 2008/0306444 A1 | 12/2008 | Brister et al. |
| 2008/0312512 A1 | 12/2008 | Brukalo et al. |
| 2008/0312634 A1 | 12/2008 | Helmerson et al. |
| 2008/0319381 A1 | 12/2008 | Yodfat et al. |
| 2008/0319383 A1 | 12/2008 | Byland et al. |
| 2008/0319384 A1 | 12/2008 | Yodfat et al. |
| 2008/0319394 A1 | 12/2008 | Yodfat et al. |
| 2008/0319414 A1 | 12/2008 | Yodfat et al. |
| 2008/0319416 A1 | 12/2008 | Yodfat et al. |
| 2009/0036760 A1 | 2/2009 | Hayter |
| 2009/0036870 A1 | 2/2009 | Mounce et al. |
| 2009/0043291 A1 | 2/2009 | Thompson |
| 2009/0048584 A1 | 2/2009 | Thompson |
| 2009/0069745 A1 | 3/2009 | Estes et al. |
| 2009/0069746 A1 | 3/2009 | Miller et al. |
| 2009/0069749 A1 | 3/2009 | Miller et al. |
| 2009/0069784 A1 | 3/2009 | Estes et al. |
| 2009/0069785 A1 | 3/2009 | Miller et al. |
| 2009/0069787 A1 | 3/2009 | Estes et al. |
| 2009/0076453 A1 | 3/2009 | Mejlhede et al. |
| 2009/0076849 A1 | 3/2009 | Diller |
| 2009/0082728 A1 | 3/2009 | Bikovsky |
| 2009/0093756 A1 | 4/2009 | Minaie et al. |
| 2009/0099507 A1 | 4/2009 | Koops |
| 2009/0105636 A1 | 4/2009 | Hayter et al. |
| 2009/0112333 A1 | 4/2009 | Sahai |
| 2009/0118664 A1 | 5/2009 | Estes et al. |
| 2009/0143916 A1 | 6/2009 | Boll et al. |
| 2009/0164190 A1 | 6/2009 | Hayter |
| 2009/0177142 A1 | 7/2009 | Blomquist et al. |
| 2009/0177154 A1 | 7/2009 | Blomquist |
| 2009/0192722 A1 | 7/2009 | Shariati et al. |
| 2009/0198191 A1 | 8/2009 | Chong et al. |
| 2009/0198215 A1 | 8/2009 | Chong et al. |
| 2009/0221890 A1 | 9/2009 | Saffer et al. |
| 2010/0010330 A1 | 1/2010 | Rankers et al. |
| 2010/0049164 A1* | 2/2010 | Estes ............... A61M 5/1723 604/504 |

(56) References Cited

U.S. PATENT DOCUMENTS

| | | |
|---|---|---|
| 2010/0057040 A1 | 3/2010 | Hayter |
| 2010/0057041 A1 | 3/2010 | Hayter |
| 2010/0094078 A1 | 4/2010 | Weston |
| 2010/0121167 A1 | 5/2010 | Mcgarraugh |
| 2010/0165795 A1 | 7/2010 | Elder et al. |
| 2010/0168538 A1 | 7/2010 | Keenan et al. |
| 2010/0168820 A1 | 7/2010 | Maniak et al. |
| 2010/0174229 A1 | 7/2010 | Hsu |
| 2010/0174266 A1 | 7/2010 | Estes |
| 2010/0179409 A1 | 7/2010 | Kamath et al. |
| 2010/0211005 A1 | 8/2010 | Edwards et al. |
| 2010/0249530 A1* | 9/2010 | Rankers ............... A61B 5/14532 600/300 |
| 2010/0273738 A1 | 10/2010 | Valcke et al. |
| 2010/0286601 A1 | 11/2010 | Yodfat et al. |
| 2010/0286653 A1 | 11/2010 | Kubel et al. |
| 2010/0298685 A1 | 11/2010 | Hayter |
| 2010/0298765 A1 | 11/2010 | Budiman et al. |
| 2010/0324382 A1 | 12/2010 | Cantwell et al. |
| 2010/0324977 A1 | 12/2010 | Dragt |
| 2010/0325864 A1 | 12/2010 | Briones et al. |
| 2011/0009813 A1 | 1/2011 | Rankers |
| 2011/0015511 A1 | 1/2011 | Bousamra et al. |
| 2011/0040247 A1 | 2/2011 | Mandro et al. |
| 2011/0071464 A1 | 3/2011 | Palerm |
| 2011/0098637 A1 | 4/2011 | Hill |
| 2011/0098674 A1 | 4/2011 | Vicente et al. |
| 2011/0105955 A1 | 5/2011 | Yudovsky et al. |
| 2011/0106050 A1 | 5/2011 | Yodfat et al. |
| 2011/0118699 A1 | 5/2011 | Yodfat et al. |
| 2011/0124996 A1* | 5/2011 | Reinke ............... A61M 5/14248 600/365 |
| 2011/0130716 A1 | 6/2011 | Estes et al. |
| 2011/0163880 A1 | 7/2011 | Halff et al. |
| 2011/0199194 A1 | 8/2011 | Waldock et al. |
| 2011/0224523 A1 | 9/2011 | Budiman |
| 2011/0313390 A1 | 12/2011 | Roy et al. |
| 2011/0319813 A1 | 12/2011 | Kamen et al. |
| 2012/0016304 A1 | 1/2012 | Patel et al. |
| 2012/0029468 A1 | 2/2012 | Diperna et al. |
| 2012/0046606 A1 | 2/2012 | Arefieg |
| 2012/0065894 A1 | 3/2012 | Tubb et al. |
| 2012/0078067 A1 | 3/2012 | Kovatchev et al. |
| 2012/0123234 A1 | 5/2012 | Atlas et al. |
| 2012/0150556 A1 | 6/2012 | Galasso et al. |
| 2012/0172694 A1 | 7/2012 | Desborough et al. |
| 2012/0172802 A1 | 7/2012 | Blomquist |
| 2012/0185267 A1 | 7/2012 | Kamen et al. |
| 2012/0197207 A1 | 8/2012 | Stefanski |
| 2012/0203467 A1 | 8/2012 | Kamath et al. |
| 2012/0209208 A1 | 8/2012 | Stefanski |
| 2012/0227737 A1 | 9/2012 | Mastrototaro et al. |
| 2012/0238851 A1 | 9/2012 | Kamen et al. |
| 2012/0238853 A1 | 9/2012 | Arefieg |
| 2012/0238999 A1 | 9/2012 | Estes et al. |
| 2012/0245448 A1 | 9/2012 | Shariati et al. |
| 2012/0245556 A1 | 9/2012 | Kovatchev et al. |
| 2012/0245855 A1 | 9/2012 | Kamath et al. |
| 2012/0246106 A1 | 9/2012 | Atlas et al. |
| 2012/0259191 A1 | 10/2012 | Shariati et al. |
| 2012/0277723 A1 | 11/2012 | Skladnev et al. |
| 2012/0283694 A1 | 11/2012 | Yodfat et al. |
| 2012/0289931 A1 | 11/2012 | Robinson et al. |
| 2012/0302991 A1 | 11/2012 | Blomquist et al. |
| 2012/0323590 A1 | 12/2012 | Udani |
| 2012/0330270 A1 | 12/2012 | Colton |
| 2013/0046281 A1 | 2/2013 | Javitt |
| 2013/0053818 A1 | 2/2013 | Estes |
| 2013/0053819 A1 | 2/2013 | Estes |
| 2013/0053820 A1 | 2/2013 | Estes et al. |
| 2013/0102867 A1 | 4/2013 | Desborough et al. |
| 2013/0116649 A1 | 5/2013 | Breton et al. |
| 2013/0138205 A1 | 5/2013 | Kushwaha et al. |
| 2013/0159456 A1 | 6/2013 | Daoud et al. |
| 2013/0165041 A1 | 6/2013 | Bukovjan et al. |
| 2013/0204186 A1 | 8/2013 | Moore et al. |
| 2013/0204202 A1 | 8/2013 | Trombly et al. |
| 2013/0218126 A1 | 8/2013 | Hayter et al. |
| 2013/0237932 A1 | 9/2013 | Thueer et al. |
| 2013/0245563 A1 | 9/2013 | Mercer et al. |
| 2013/0245604 A1 | 9/2013 | Kouyoumjian et al. |
| 2013/0253418 A1 | 9/2013 | Kamath et al. |
| 2013/0275139 A1 | 10/2013 | Coleman |
| 2013/0281965 A1 | 10/2013 | Kamen et al. |
| 2013/0297334 A1 | 11/2013 | Galasso et al. |
| 2013/0338629 A1 | 12/2013 | Agrawal et al. |
| 2013/0338630 A1 | 12/2013 | Agrawal et al. |
| 2013/0345663 A1 | 12/2013 | Agrawal et al. |
| 2014/0005633 A1 | 1/2014 | Finan |
| 2014/0025015 A1 | 1/2014 | Cross et al. |
| 2014/0031759 A1 | 1/2014 | Kouyoumjian et al. |
| 2014/0039383 A1 | 2/2014 | Dobbles et al. |
| 2014/0052091 A1 | 2/2014 | Dobbles et al. |
| 2014/0052092 A1 | 2/2014 | Dobbles et al. |
| 2014/0052093 A1 | 2/2014 | Dobbles et al. |
| 2014/0052094 A1 | 2/2014 | Dobbles et al. |
| 2014/0052095 A1 | 2/2014 | Dobbles et al. |
| 2014/0066884 A1 | 3/2014 | Keenan et al. |
| 2014/0066885 A1 | 3/2014 | Keenan et al. |
| 2014/0066886 A1 | 3/2014 | Roy et al. |
| 2014/0066887 A1 | 3/2014 | Mastrototaro et al. |
| 2014/0066888 A1 | 3/2014 | Parikh et al. |
| 2014/0066889 A1 | 3/2014 | Grosman et al. |
| 2014/0066890 A1 | 3/2014 | Sloan et al. |
| 2014/0066892 A1 | 3/2014 | Keenan et al. |
| 2014/0088557 A1 | 3/2014 | Mernoe et al. |
| 2014/0094766 A1 | 4/2014 | Estes et al. |
| 2014/0107607 A1 | 4/2014 | Estes |
| 2014/0114278 A1 | 4/2014 | Dobbles et al. |
| 2014/0121635 A1 | 5/2014 | Hayter |
| 2014/0128705 A1 | 5/2014 | Mazlish |
| 2014/0128803 A1 | 5/2014 | Dobbles et al. |
| 2014/0180203 A1 | 6/2014 | Budiman et al. |
| 2014/0180240 A1 | 6/2014 | Finan et al. |
| 2014/0228627 A1 | 8/2014 | Soffer et al. |
| 2014/0228668 A1 | 8/2014 | Wakizaka et al. |
| 2014/0235981 A1 | 8/2014 | Hayter |
| 2014/0249500 A1 | 9/2014 | Estes |
| 2014/0276553 A1 | 9/2014 | Rosinko et al. |
| 2014/0276554 A1 | 9/2014 | Finan et al. |
| 2014/0276555 A1 | 9/2014 | Morales |
| 2014/0276583 A1 | 9/2014 | Chen et al. |
| 2014/0309615 A1 | 10/2014 | Mazlish |
| 2014/0323959 A1 | 10/2014 | Lebel et al. |
| 2015/0018633 A1 | 1/2015 | Kovachev et al. |
| 2015/0025471 A1 | 1/2015 | Enggaard |
| 2015/0025495 A1 | 1/2015 | Peyser |
| 2015/0030641 A1 | 1/2015 | Anderson et al. |
| 2015/0045737 A1 | 2/2015 | Stefanski |
| 2015/0073337 A1 | 3/2015 | Saint et al. |
| 2015/0080789 A1 | 3/2015 | Estes et al. |
| 2015/0120323 A1 | 4/2015 | Galasso et al. |
| 2015/0136336 A1 | 5/2015 | Huang |
| 2015/0148774 A1 | 5/2015 | Yao |
| 2015/0157794 A1 | 6/2015 | Roy et al. |
| 2015/0164414 A1 | 6/2015 | Matthews |
| 2015/0165119 A1 | 6/2015 | Palerm et al. |
| 2015/0217051 A1 | 8/2015 | Mastrototaro et al. |
| 2015/0217052 A1 | 8/2015 | Keenan et al. |
| 2015/0265767 A1 | 9/2015 | Vazquez et al. |
| 2015/0265768 A1 | 9/2015 | Vazquez et al. |
| 2015/0314062 A1 | 11/2015 | Blomquist et al. |
| 2015/0320933 A1 | 11/2015 | Estes |
| 2015/0328402 A1 | 11/2015 | Nogueira et al. |
| 2015/0351683 A1 | 12/2015 | Brauker et al. |
| 2015/0352282 A1 | 12/2015 | Mazlish |
| 2015/0352283 A1 | 12/2015 | Galasso |
| 2016/0000998 A1 | 1/2016 | Estes |
| 2016/0030669 A1 | 2/2016 | Harris et al. |
| 2016/0038673 A1 | 2/2016 | Morales |
| 2016/0082187 A1 | 3/2016 | Schaible et al. |
| 2016/0082188 A1 | 3/2016 | Blomquist et al. |
| 2016/0158438 A1 | 6/2016 | Monirabbasi et al. |
| 2016/0162662 A1 | 6/2016 | Monirabbasi et al. |

(56) References Cited

U.S. PATENT DOCUMENTS

| | | | |
|---|---|---|---|
| 2016/0213841 A1 | 7/2016 | Geismar et al. | |
| 2016/0256629 A1 | 9/2016 | Grosman et al. | |
| 2017/0182248 A1 | 6/2017 | Rosinko | |
| 2017/0189614 A1 | 7/2017 | Mazlish et al. | |
| 2017/0203036 A1 | 7/2017 | Mazlish et al. | |

FOREIGN PATENT DOCUMENTS

| | | |
|---|---|---|
| DE | 10236669 | 2/2004 |
| DK | PA200401893 | 12/2004 |
| DK | PA 200401893 | 12/2004 |
| EP | 0062974 | 10/1982 |
| EP | 0275213 | 7/1988 |
| EP | 0496141 | 7/1992 |
| EP | 0612004 | 8/1994 |
| EP | 0580723 | 10/1995 |
| EP | 1045146 | 10/2000 |
| EP | 1136698 | 9/2001 |
| EP | 1177802 | 2/2002 |
| EP | 0721358 | 5/2002 |
| EP | 1495775 | 1/2005 |
| EP | 1527792 | 5/2005 |
| EP | 1754498 | 2/2007 |
| EP | 1818664 | 8/2007 |
| FR | 2585252 | 1/1987 |
| GB | 0747701 | 4/1956 |
| GB | 2218831 | 11/1989 |
| JP | H09504974 | 5/1997 |
| JP | 2000513974 | 10/2000 |
| JP | 2002-085556 A | 3/2002 |
| JP | 2002507459 | 3/2002 |
| JP | 2002523149 | 7/2002 |
| JP | 2003-531691 A | 10/2003 |
| JP | 2010-502361 A | 1/2010 |
| JP | 2010-524639 A | 7/2010 |
| WO | WO 1990015928 | 12/1990 |
| WO | WO 1997021457 | 6/1997 |
| WO | WO 1998004301 | 2/1998 |
| WO | WO 1998011927 | 3/1998 |
| WO | WO 1998057683 | 12/1998 |
| WO | WO 1999021596 | 5/1999 |
| WO | WO 1999039118 | 8/1999 |
| WO | WO 1999048546 | 9/1999 |
| WO | WO 2001054753 | 8/2001 |
| WO | WO 2001072360 | 10/2001 |
| WO | WO 2001091822 | 12/2001 |
| WO | WO 2001091833 | 12/2001 |
| WO | WO 2002040083 | 5/2002 |
| WO | WO 2002057627 | 7/2002 |
| WO | WO 2002068015 | 9/2002 |
| WO | WO 2002084336 | 10/2002 |
| WO | WO 2002100469 | 12/2002 |
| WO | WO 2003026726 | 4/2003 |
| WO | WO 2003103763 | 12/2003 |
| WO | WO 2004056412 | 7/2004 |
| WO | WO 2004110526 | 12/2004 |
| WO | WO 2005002652 | 1/2005 |
| WO | WO 2005039673 | 5/2005 |
| WO | WO 2005072794 | 8/2005 |
| WO | WO 2005072795 | 8/2005 |
| WO | WO 2006067217 | 6/2006 |
| WO | WO 2006097453 | 9/2006 |
| WO | WO 2006105792 | 10/2006 |
| WO | WO 2006105793 | 10/2006 |
| WO | WO 2006105794 | 10/2006 |
| WO | WO 2007141786 | 12/2007 |
| WO | 2008/134146 A1 | 11/2008 |

OTHER PUBLICATIONS

Asante Solutions Pearl User Manual, Asante Inc., 2012, 180 pages.
Collins and Lee, "Microfluidic flow transducer based on the measurement of electrical admittance," Lab Chip, 2004 4 pages.
Debiotech News Release, "Debiotech reveals its new miniaturized Disposable Insulin Nanopump™ for Diabetes therapy," available at http://www.debiotech.com/news/nw_159.html Apr. 24, 2006, 3 pages.
International Search Report and Written Opinion in International Application No. PCT/US2014/67665, dated Apr. 21, 2015, 13 pages.
Medtronic News Release, "Medtronic Receives FDA Approval for World's First Insulin Pump with Real-time Continuous Glucose Monitoring," Apr. 13, 2006, 3 pages.
OmniPod Insulin Management System—Investor Relations—Press Release, Feb. 1, 2005, http://investors.insulet.com/phoenix.zhtml?c=209336&p=irol-newsArticle&ID=988708&highlight= 1 page.
OmniPod Quick Start Guide, 2007, 2 pages.
Patent Abstracts of Japan, vol. 1999, No. 04, and JP 11 010036, Apr. 30, 1999 and Jan. 19, 1999, Toray Ind. Inc.
The Medtronic Diabetes Connection, 2006, 6 pages.
Xilas Temp Touch, "The latest in high-tech and convenient devices," DOCNews, vol. 2, No. 7, Jul. 1, 2005, http://docnews.diabetesjournals.ord/cgi/content/full/2/7/13, 3 pages.

* cited by examiner

INFUSION PUMP SYSTEM AND METHOD

CROSS-REFERENCE TO RELATED APPLICATIONS

This application is a continuation of U.S. application Ser. No. 14/094,185, filed Dec. 2, 2013, now U.S. Pat. No. 10,569,015, issued Feb. 25, 2020, the entire contents of which are hereby incorporated by reference.

TECHNICAL FIELD

This document relates to an infusion pump system, such as a portable infusion pump system for dispensing insulin or another medicine.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

Users of infusion pump devices often need to communicate with the infusion pump via a user interface to control the operations of the infusion pump in a safe and effective manner. For example, a user may press a series of buttons on the user interface to enter food intake data into the infusion pump, such as a number of grams of carbohydrates that is indicative of a recently or soon-to-be consumed meal. The food intake data can be used in conjunction with other parameters stored by the infusion pump system to calculate a suggested bolus dosage of insulin based on the grams of carbohydrates entered by the user. In another example, a user may enter information into the infusion pump system via a user interface that indicates that the user is going to perform a level of physical exercise. In some circumstances, the infusion pump system may reduce the amount of a planned dispensation of insulin in response to the exercise information entered by the user.

SUMMARY

Some embodiments of an infusion pump system may be configured to receive user input at the infusion pump system using voice input. Some such embodiments can interpret the user's voice input using speech recognition technology, and in response to the user's voice input, the infusion pump system can automatically perform one or more tasks (e.g., without additional user intervention). By incorporating speech recognition equipment within the infusion pump system, user communications with the pump system can be enhanced and simplified. In particular embodiments, the infusion pump system may further include a capability to perform natural language processing of the user's voice input, thereby providing an infusion pump system configured to correlate any one of a number of spoken phrases into selected tasks. In addition or in the alternative, some embodiments of an infusion pump system may be configured to allow the user to provide input to the infusion pump system using photographic images. For example, the user may take a photo of a soon-to-be-consumed meal, and the photo may be provided as food intake data that is input to the infusion pump system for purposes of performing one or more tasks by the infusion pump system. In response, the infusion pump system may, for example, use image recognition technology to estimate the carbohydrate and other nutritional contents of the food depicted in the photo and then suggest a particular bolus dosage of insulin (or other medicine) corresponding to the food in the photo.

In particular embodiments described herein, a medical infusion pump system may include a portable housing that defines a space to receive a medicine. The system may also include a pump drive system to dispense medicine from the portable housing when the medicine is received in the space. In some embodiments, the system may also include control circuitry that communicates control signals to the pump drive system to control dispensation of the medicine from the portable housing. The system may also include a speech recognition system that is in communication with the control circuitry. The control circuitry may select one or more tasks to be performed by the infusion pump system in response to the speech recognition system receiving a user's voice input.

In some embodiments of the medical infusion pump system that includes the speech recognition system, at least a portion of the speech recognition system may be stored in one or more computer-readable memory devices at a remote server system, and the control circuitry may be configured to communicate with the remote server system to use the speech recognition system. Optionally, at least a portion of the speech recognition system may be disposed in the portable housing. Further, the control circuitry may be housed in a controller housing that is removably attachable to the portable housing, and at least a portion of the speech recognition system may be disposed in the controller housing. In some embodiments, the speech recognition system may optionally comprise a first subsystem and a second subsystem. At least a portion of the first subsystem may be stored in one or more computer-readable memory devices at a remote server system that communicates with the control circuitry. In addition, at least a portion of the second subsystem may be stored in one or more computer-readable memory devices in the portable housing or in a controller device housing in which the control circuitry is housed and that is removably attachable to the portable housing. In some embodiments, the medical infusion pump system may also include a voice synthesizer for outputting audible human language communications from the infusion pump system. In particular embodiments, the medical infusion pump system may include a remote control device that is separate from the portable housing and that houses the control circuitry. The remote control device may be configured to wirelessly communicate with a wireless communication device housed in the portable housing, and the remote control device may include a microphone for receiving the voice input. Further, in some embodiments the medical infusion pump optionally includes a voice synthesizer for outputting audible human language communications from the remote control device.

In particular embodiments described herein, a medical infusion pump system may include a portable housing that defines a space to receive a medicine. The system may also include a pump drive system to dispense medicine from the portable housing when the medicine is received in the space. In some embodiments, the system may also include control circuitry that communicates control signals to the pump drive system to control dispensation of the medicine from the portable housing. The system may also include an image recognition system in communication with the control circuitry. The control circuitry may select one or more tasks to be performed by the infusion pump system in response to the image recognition system receiving user input comprising a user-provided digital image.

In some embodiments of the medical infusion pump system that includes the image recognition system, at least a portion of the image recognition system may be stored in one or more computer-readable memory devices at a remote server system, and the control circuitry may be configured to communicate with the remote server system to use the image recognition system. In particular embodiments, at least a portion of the image recognition system may be disposed in the portable housing. Optionally, the control circuitry may be housed in a controller housing that is removably attachable to the portable housing, and at least a portion of the image recognition system may be disposed in the controller housing. In some embodiments, the image recognition system may comprise a first subsystem and a second subsystem. At least a portion of the first subsystem may be stored in one or more computer-readable memory devices at a remote server system that communicates with the control circuitry, and at least a portion of the second subsystem may be stored in one or more computer-readable memory devices in the portable housing or in a controller device housing in which the control circuitry is housed and that is removably attachable to the portable housing. Optionally, the medical infusion pump system that includes the image recognition system may include a voice synthesizer for outputting audible human language communications from the infusion pump system. The system may also optionally include a remote control device that is separate from the portable housing and that houses the control circuitry. The remote control device may be configured to wirelessly communicate with a wireless communication device housed in the portable housing, and the remote control device may include a camera device for receiving the digital image. Some such embodiments may include a voice synthesizer for outputting audible human language communications from the remote control device.

Some embodiments described herein may include a method of controlling a portable infusion pump system. The method may include receiving a user's voice input that is indicative of a task associated with using a portable infusion pump system, and controlling the portable infusion pump system to change an operation of the portable infusion pump system based upon the user's voice input. The method may optionally include, prompting a user via a user interface display to confirm the operation change of the portable infusion pump system in response to receiving the user's voice input. In some embodiments, the operation change may optionally comprise calculating or initiating a bolus dispensation of a medicine from the portable infusion pump system.

Some embodiments described herein may include another method of controlling a portable infusion pump system. The method may include receiving user input comprising a digital image that is indicative of a food item consumed or to be consumed by the user of the portable infusion pump system, and controlling the portable infusion pump system to change an operation of the portable infusion pump system based upon the user input comprising the digital image. The method may optionally include, prompting a user via a user interface display to confirm the operation change of the portable infusion pump system in response to receiving the user input comprising the digital image. In some embodiments, the operation change may optionally comprise calculating or initiating a bolus dispensation of a medicine from the portable infusion pump system.

Some or all of the embodiments described herein may provide one or more of the following advantages. First, some embodiments of the infusion pump system may be configured to receive user input via speech recognition technology. Second, some embodiments of the infusion pump system may be configured to receive user input via image recognition technology. Third, some embodiments of an infusion pump system equipped with speech or image recognition technology may facilitate convenient user input of information to the infusion pump system. Third, the safety and efficacy of an infusion pump system may be enhanced because the convenient manner of inputting data to the infusion pump using speech or image recognition may facilitate more timely and complete data entry by the user. Fourth, in some circumstances, some users who may be unable (mentally or physically) to reliably operate a conventional push-button user interface of an infusion pump system may instead be served by embodiments of the system described herein, which can permit such users to reliably input data to an infusion pump system using the speech or image recognition communication interface. Fifth, the infusion pump system equipped with speech or image recognition capabilities may be configured to be portable, wearable, and (in some circumstances) concealable. For example, a user can conveniently wear the infusion pump system on the user's skin under clothing or can carry the pump system in the user's pocket (or other portable location) while receiving the medicine dispensed from the pump device.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
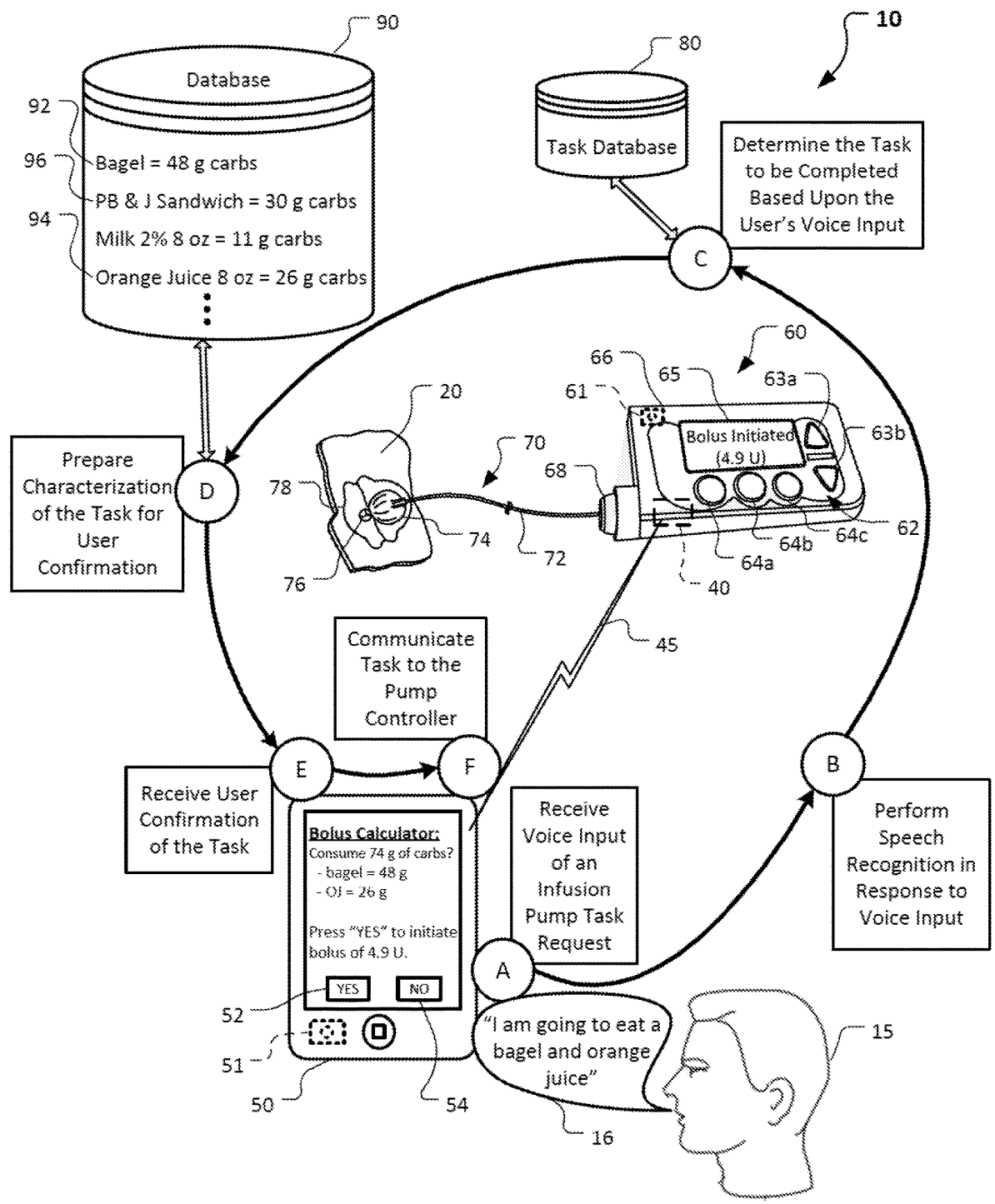
FIG. 1 is a diagram depicting the use of an infusion pump system equipped with speech recognition capabilities, in accordance with some embodiments.

Referring to FIG. 1, some embodiments of an infusion pump system 10 can include speech recognition equipment for purposes of receiving and responding to a user's voice input. The infusion pump system 10 may include, among other elements, a control device 50 and a pump device 60 that receives communications from the control device 50. In the embodiment depicted in FIG. 1, the control device 50 wirelessly communicates with the pump device 60, but the system 10 can be implemented using a control device that is removably attached to a corresponding pump device (e.g., for hard-wired electrical communication) or using a control device that is housed together with the pump device (e.g., in a single portable construct). In one example, the infusion pump system 10 can be configured to perform a series of steps A through F in response to a user's voice input 16. By incorporating voice recognition capabilities within the infusion pump system 10, user communications with the portable pump 60 can be enhanced and simplified. As a result, the accuracy and completeness of the data entered by the user into the portable pump 60 can be improved, and the user may experience greater convenience and time efficiency during interactions with the infusion pump system 10.

In this embodiment, the infusion pump system 10 includes the remote control device 50 in communication with the portable pump 60, which is used to dispense insulin or another medication to a user 15 via an infusion set 70 attached to and penetrating the user's skin 20. In some embodiments, the portable pump 60 optionally includes a user interface 62 comprised of input devices such as buttons 63a, 63b, 64a, 64b, 64c and output devices such as display 65. In addition, in this embodiment the user 15 can communicate with the infusion pump system 10 by providing voice input, such as the example verbal statement 16 depicted in FIG. 1. Such a verbal statement can be received by voice recognition equipment housed in the control device 50, in the pump device 60, or both. In particular embodiments, the portable pump 60 may also include a wireless communications circuit 40 that facilitates short-range wireless communications 45 between the internal control circuitry of the portable pump 60 and the external remote control device 50.

The infusion pump system 10 is configured to controllably dispense a medicine to be infused into the tissue or vasculature of a targeted individual, such as a human or animal patient. In some embodiments, the portable pump 60 includes the housing structure 66 that defines a cavity in which a fluid cartridge (not shown) can be slidably received. For example, the fluid cartridge can be a carpule that is either user-fillable or is preloaded with insulin or another medicine for use in the treatment of Diabetes (e.g., Byetta®, Symlin®, or others). Such a cartridge may be supplied, for example, by Eli Lilly and Co. of Indianapolis, Ind. Other examples of medicines that can be contained in the fluid cartridge include: pain relief drugs, hormone therapy, blood pressure treatments, anti-emetics, osteoporosis treatments, or other injectable medicines. The fluid cartridge may have other configurations. For example, in some embodiments the fluid cartridge may comprise a reservoir that is integral with the pump housing structure 66 (e.g., the fluid cartridge can be defined by one or more walls of the pump housing structure 66 that surround a plunger to define a reservoir in which the medicine is injected or otherwise received).

Still referring to FIG. 1, in this embodiment, the portable pump 60 optionally includes a cap device 68 to retain the fluid cartridge in the cavity of the housing structure 66 and to penetrate a septum of the fluid cartridge for purposes of establishing fluid communication with the infusion set 70. The portable pump 60 includes a drive system that advances a plunger (not shown in FIG. 1) in the fluid cartridge so as to dispense fluid therefrom. In some embodiments, the dispensed fluid exits the fluid cartridge, passes through a flexible tube 72 of the infusion set 70 to a cannula housing 74 retained to the user's skin 20 by a skin adhesive patch 78. The dispensed fluid can enter through the skin 20 via a cannula 76 attached to the underside of the cannula housing 74.

In some embodiments, the infusion pump system 10 can be configured to supply scheduled basal dosages of insulin (or another medication) along with user-selected bolus dosages. The basal delivery rate can be selected to maintain a user's blood glucose level in a targeted range during normal activity throughout the day. The user-selected bolus deliveries may provide substantially larger amounts of insulin in particular circumstances in which the user consumed (or will consume) carbohydrates (e.g., during a meal) or in which the user's blood glucose level requires a significant downward correction. In some embodiments, the infusion pump system 10 can suggest a bolus dosage to the user in a manner that accounts for the user's food intake, the user's recent blood glucose level (e.g., manually input into the portable pump 60 by the user, detected from an integral blood test strip analyzer, wirelessly transmitted to the portable pump 60 from an external blood strip reader device, wirelessly transmitted to the portable pump 60 from an body-worn continuous glucose monitoring device, or the like), the rate of change in the user's blood glucose level, and previously delivered insulin that has not acted on the user. For example, a user can enter a carbohydrate value indicative of a meal into the portable pump 60, and in response thereto, the portable pump 60 can output a suggested bolus dosage to the user. In another example, as will be described further below, the user can provide a voice input that identifies food items that the user will consume, and the infusion pump system 10 can use speech recognition technology to determine a suggested bolus dosage that corresponds to the food items.

In some embodiments, the infusion pump system 10 may modify a bolus suggestion (e.g., a bolus delivery in conjunction with a meal) in response to certain circumstances. For example, the infusion pump system 10 may decrease or otherwise modify a post-meal bolus delivery based on a rapidly falling blood glucose level, a current blood glucose level that is below a threshold limit, based on an increased level of physical activity, or the like.

The infusion pump system 10 can be configured to be portable and can be wearable and concealable. For example, a user can conveniently wear some or all of the infusion pump system 10 on the user's skin (e.g., using skin adhesive) underneath the user's clothing or carry the portable pump 60 or remote control device 50 in the user's pocket (or other portable location) while receiving the medicine dispensed from the infusion pump system 10. As such, the pump system 10 can be used to deliver medicine to the tissues or vasculature of the user in a portable, concealable, and discrete manner.

Still referring to FIG. 1, the portable pump 60 includes the user interface 62 that permits a user to monitor and control the operation of the infusion pump system 10. In some embodiments, the user interface 62 includes a display 65 and the user-selectable buttons (e.g., five buttons 63a, 63b, 64a, 64b, and 64c in this embodiment) that are in electrical communication with the control circuitry of the portable pump 60. For example, the display 65 may be used to communicate a number of status indicators, alarms, settings, and/or menu options for the infusion pump system 10. In some embodiments, the user may press one or more of the buttons 63a, 63b, 64a, 64b, and 64c to shuffle through a number of menus or program screens that show particular status indicators, settings, and/or data (e.g., review data that shows the medicine dispensing rate, the amount of medicine delivered during the last bolus, the delivery time of the last bolus, the total amount of medicine dispensed in a given time period, the amount of medicine scheduled to be dispensed at a particular time or date, the approximate amount of medicine remaining in the cartridge, or the like).

In some embodiments, the user can adjust the settings or otherwise program the portable pump 60 by pressing one or more buttons 63a, 63b, 64a, 64b, and 64c of the user interface 62. For example, in embodiments of the infusion pump system 10 configured to dispense insulin, the user may press one or more of the buttons 63a, 63b, 64a, 64b, and 64c to change the dispensation rate of insulin or to request that a bolus of insulin be dispensed immediately, at a scheduled later time, over a period of time, or following a particular time-based profile. In another example, the user may use the buttons 63a, 63b, 64a, 64b, and 64c to manually input information such as the user's current blood glucose level (e.g., as measured by an external blood glucose meter), the current rate of change in the user's blood glucose level, or the like into the portable pump 60.

As an alternative to, or in conjunction with, pressing one or more buttons 63a, 63b, 64a, 64b, and 64c of the user interface 62 to adjust or program the infusion pump system 10, the example infusion pump system 10 can receive voice input from the user. The use of speech recognition equipment (housed in the control device 50, in the pump device 60, or both) provides an additional functionality that can enhance and simplify user interactions with the portable pump 60. For instance, using speech recognition, the need to manually actuate multiple buttons 63a, 63b, 64a, 64b, and 64c in a specific order for purposes shuffling through menus may be eliminated or otherwise reduced in some circumstances. In one example, as depicted in FIG. 1, the user of infusion pump system 10 has consumed, or will soon consume, a bagel and orange juice. As such, the user can cause the infusion pump system to initiate a task in response to the voice input (dispensing a corresponding bolus of insulin to counteract the effects of the intake of the bagel and orange juice). The bolus dispensation of insulin may be intended to cause the user's blood glucose level to remain within a target range. To begin the process, the user 15 can speak the statement 16 that identifies the food to be consumed. Such a verbal statement can be received by a component of the voice recognition equipment, such as a microphone device 51 housed in the control device 50 (or, optionally, a component of the voice recognition equipment housed in the pump device 60, such as a microphone device 61). In response to receiving the voice input, the infusion pump system 10 can interpret the statement 16, determine a recommended bolus dispensation, and present the recommendation to the user 15 for confirmation. Upon receipt of user confirmation, the infusion pump system 10 initiates or schedules the bolus dispensation task. By incorporating such voice recognition capabilities within the infusion pump system 10, user communications with the portable pump 60 can be enhanced and simplified. As a result, the accuracy and completeness of the data entered by the user into the portable pump 60 can be improved, and the user can experience greater convenience and time efficiency.

Still referring to FIG. 1, in this example at step A, the user 15 speaks the statement 16 that reflects a task or set of tasks that the user 15 wants the infusion pump system 10 to perform. For example, the user 15 makes the statement 16, "I am going to eat a bagel and orange juice." As will be described further, the infusion pump system 10 will receive and process the statement 16 and recommend a bolus dispensation of insulin to compensate for the bagel and orange juice to be consumed by the user 15.

In this example, the user 15 has made a statement 16 that identifies types of food that will be consumed, but it should be understood from the description herein that many other types of statements corresponding to other infusion pump tasks can be similarly initiated using voice input. For instance, in other non-limiting examples of the types of statements that can be made to initiate tasks, the user 15 may speak a command to "stop the pump," "start the pump," or "stop the bolus." Further, the user 15 may speak a command to "start a temporary basal rate of 50% for 3 hours," or "I am going to exercise for 1 hour." In still further examples, the user 15 may speak commands such as: "prime the infusion set," "my blood glucose level is 130," "I am going to sleep now," "display estimated battery life," "display estimated medicine expiration time," "snooze all alerts for 30 minutes," "how much insulin do I have on board," "how long have I been using this infusion set," "what time is it," "change to basal pattern B," "change to my weekend basal pattern," "soccer practice starts in 30 minutes" (which would be linked to a particular pre-programmed temporary basal pattern), "give that bolus as a square-wave bolus," "give that bolus as a 4-hour combo bolus," "remind me to bolus in an hour," "remind me to check my blood sugar in an hour," "remind me to eat lunch at 11:30," "blocked set alarm acknowledged," and the like. It should be recognized that the user 15 can provide a wide variety of types of statements to initiate a wide variety of tasks by the infusion pump system 10, and that the examples provided here are merely illustrative. In some embodiments, as will be described further in reference to FIG. 5, a natural language processing module can be implemented in infusion pump system 10 to further enhance the speech recognition capabilities of the infusion pump system 10.

Still referring to FIG. 1, in this example, the verbal statement 16 is received by the microphone 51 of the remote control device 50. In some embodiments, the user may press a button on the control device 50 or otherwise prompt the control device 50 to prepare for receiving the voice input. The remote control device 50 can include electronic circuitry for converting the statement 16 to an audio signal (e.g., an "audio file," "waveform," or "sample") that corresponds to the statement 16. The audio signal corresponding to the statement 16 can be saved (temporarily or permanently) in a computer-readable memory device housed in the control device 50, a computer-readable memory device housed in the pump device 60, or both.

In this embodiment the control device 50 is depicted as a smart phone device, but it should be understood from the description herein that, in other embodiments, the control device 50 can be implemented in the form of devices other than a smart phone device. Some other example devices that can be used similarly to the remote control device 50 can include, but are not limited to, a personal computer, a tablet computing device, a blood glucose meter device (e.g., an external blood strip reader), a continuous glucose meter device, a wearable computing device, a PDA, or a custom remote device. In still other embodiments, the control device is not a remote device, but instead is included as part of, or mechanically attached together with, the pump device. For instance, in such embodiments the pump device of the infusion pump system can be equipped with the capabilities to perform the functions described herein in regard to the remote control device 50. Further, in some embodiments certain operations or parts of certain operations may be performed at a remote server system, including a cloud-based server system, rather than completely on a personal computing device such as the remote control device 50. Accordingly, the remote control device 50, or equivalent, can be connected to a network such as the internet or an intranet system. Such a division of tasks may provide better process optimization, computational efficiency, and response time.

Still referring to FIG. 1, in this example at step B, the infusion pump system 10 performs a speech recognition function in response to receiving the voice input 16. In some implementations, the speech recognition function provides a repeatable process of translating a voice utterance to a text transcription using an automated speech recognition ("ASR") system. In some ASR systems, acoustic and language models can be used by speech recognition engines to statistically analyze an encoded voice utterance in order to create one or more likely text strings that reflect the sounds of the speaker. Some ASR systems may use phonetic dictionaries (e.g., lists of words and their phonetic spellings) when performing speech recognition. Such phonetic dictionaries have been compiled by including pronunciation guides from standard language dictionaries, and by manually labeling acoustic examples of various words spoken by various speakers. In some embodiments, the ASR system can use a language model that includes a large vocabulary statistical language model capable of transcribing complex user utterances. Many speech recognition engines have a group of parameters that may be adjusted to change the way that a voice utterance is analyzed.

Using an ASR system in the remote control device 50, or remotely located at a server in communication with the remote control device 50, or in a combination of tasks among the remote control device 50 and at a remote server, the audio signal from the voice input 16 can be transcribed to one or more candidate text transcriptions correlating to the audio signal of statement 16. In some embodiments, the control device 50 can generate speech recognition confidence values for the candidate transcriptions that are generated. In particular embodiments, the transcription with the highest confidence value may be selected by the ASR system as the designated transcription. Other techniques may also be used to create transcription(s) in response to the voice input 16, and to select which candidate transcription to use as the designated transcription. In some circumstances, no candidate transcription having a confidence value that surpasses a threshold confidence level is identified. In some such circumstances, the control device 50 may request clarification from the user 15, or may request more information from the user 15. Such requests may be presented to the user 15 audibly using voice synthesis at the remote control device 50, or visually by presenting an indication on the display of the remote control device 50, or by a combination of audible and visual indicators.

Still referring to FIG. 1, in this example at step C, the text transcription(s) of the speech recognition process from step B are compared to a compilation of tasks in a task database 80 indicative of available tasks to be performed by the infusion pump system 10. Such a comparison function (at step C) can be useful for determining the task to be performed by the pump system 10 that most likely corresponds the voice input 16 from the user 15. In some embodiments, the task database 80 is stored in a computer-readable memory device housed in the remote control device 50. However, the task database 80 can also be stored in a computer-readable memory device housed in the portable pump 60, stored in a computer-readable memory device housed at a remote server system in communication with the remote control device 50 or the portable pump 60, or at a combination of such computer-readable memory locations (e.g., a distributed database configuration). In this embodiment, the task database 80 is a repository that stores an extensive number of tasks available to be performed by the pump system corresponding to a variety of types of voice input statements, such as statement 16. The transcription(s) of the voice input from step B can be compared to the tasks listed in the task database 80 to find matching task(s) to be performed by the pump system 10. In some embodiments, a confidence level for the match between the transcription(s) and the task(s) can be determined. Optionally, the task with the highest confidence level can be automatically selected for implementation by the control device 50, the pump device 60, or both. In particular embodiments, if no task is determined at step C with a confidence level that surpasses a threshold level, or if multiple tasks have confidence levels that are within a differentiation threshold level of each other, the user 15 is prompted to verify which task should be implemented (e.g., presented in visual and/or audio output via the user interface of the control device 50 or the pump device 60 with a request for clarification or more information as described above). In some such cases, the user 15 may be presented with the task having the highest confidence level and the user 15 may be prompted to confirm that task should be implemented by the infusion pump system 10 (e.g., the prompt for verification from the user can be presented in visual and/or audio output via the user interface of the control device 50 or the pump device 60).

Still referring to FIG. 1, in this example at step D, the selected task from step C is characterized in preparation for presentation to the user 15 (for subsequent user confirmation). Depending on the task, additional information may be acquired from a database 90 as a part of the preparation step. The database 90, as with the task database 80, can be stored in one or more computer-readably memory devices housed in various locations including in the remote control device 50, the portable pump 60, a remote server including cloud-based servers, and at a combination of such locations. As depicted by this example in FIG. 1, the database 90 queried by the process at step D can contain nutritional information for a variety of food items. The nutritional information can include, but is not limited to, carbohydrates, fat, protein, and the glycemic index for food items. In some embodiments, the database 90 can also include the user's 15 most current blood glucose reading, an insulin-on-board level, an insulin sensitivity factor for the user 15, bolus delivery preference, and the like. In particular embodiments, some or all of such nutritional information and other data can be considered when the task is being prepared for presentation to the user 15. For example, in response to the statement 16, the nutritional information for a bagel 92 and orange juice 94 can be queried from the database 90. In some embodiments, the data stored in database 90 is customizable by the user 15. For example, the user 15 may make a particular food item, like a peanut butter and jelly sandwich 96, such that it has particular nutritional contents. The user's custom nutritional information can be given preference in the database 90 over the default nutritional information. In some embodiments, as part of the preparation for presenting the task to the user 15, the user 15 may first be presented with a request for additional information. For example, the user 15 may be presented with a request to input a current blood glucose level. After the receipt of such addition information, the preparation for presenting the task to the user 15 can be completed.

Still referring to FIG. 1, in this example at step E, the finalized task to be performed by the infusion pump system is presented to the user 15 for confirmation. The task may be presented to the user 15 audibly using voice synthesis at the control device 50 (or the pump device 60), or visually by presenting an indication on the display of the control device 50 (or the pump device 60), or by a combination of audible and visual indicators at one or both of the control device 50 and the pump device 60. For example, in response to the statement 16, the user 15 is presented with information indicating that the infusion pump system 10 has identified a task related to the user's 15 intent to consume 74 grams of carbohydrates (48 grams from the bagel and 26 grams from the orange juice), and that the infusion pump system 10 recommends a corresponding bolus dispensation of 4.9 Units of insulin. To confirm that task, the user 15 can select "YES" 52 on the remote control device 50. In response to a selection of the "YES" button 52, the control device 50 can communicate with the pump device 60 so as to initiate the dispensation of the bolus dosage (e.g., 4.9 Units in this example), as described below. Or to deny that task, the user 15 can select "NO" 54 on the remote control device 50. Optionally, in response to a selection of the "NO" button 54, the control device 50, can present the user with an option to manually input or verbally speak a specific number for a bolus dosage that is different from the suggested dosage displayed on the screen at step E. Alternatively, or in addition to, the manual selection of "YES" 52 or "NO" 54, the user 15 may speak "yes" or "no" to the remote control device 50 to confirm or deny the task presented.

Still referring to FIG. 1, in this example at step F, the remote control device 50 communicates the task to the portable pump 60 for activation of the portable pump 60 in accordance with the task confirmed by the user 15 (e.g., after the user selected the "YES" button 52). In the example, the display 65 of the portable pump 60 indicates that a bolus dispensation of 4.9 Units has been initiated. In this embodiment, communications between the remote control device 50 and the portable pump 60 are conducted by short-range wireless technologies such as, but not limited to, RF, Bluetooth, NFC, IR, Bluetooth low energy, ANT+, and the like. Accordingly, the portable pump 60 can include a wireless communication circuit 40 that sends and receives data in cooperation with the remote control device 50. In alternative embodiments, the communications between the remote control device 50 and the portable pump 60 can be via a hardwired connection therebetween.

Figure 2:
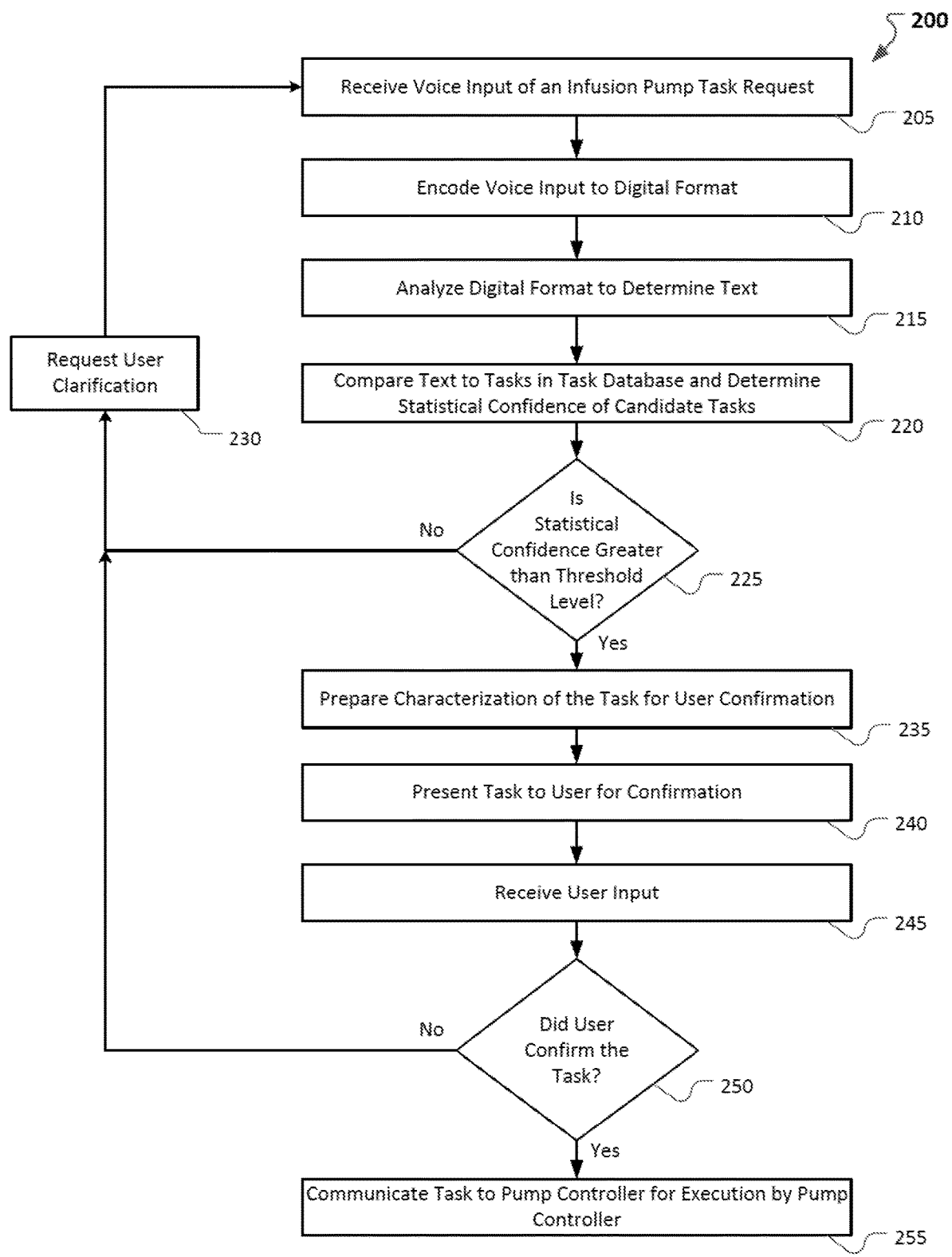
FIG. 2 is a flowchart describing a process of using an infusion pump system including with speech recognition equipment, in accordance with some embodiments.

Referring now to FIG. 2, the control circuitry of a medical device (e.g., a portable infusion pump in this embodiment) that includes speech recognition equipment can implement a process 200 of receiving voice input from a user, and controlling the medical device in accordance with task(s) associated with the voice input. Such a process 200, for example, can be implemented by the control circuitry housed in the control device 50, the portable pump 60, or a combination thereof, and other embodiments of infusion pump systems described herein (e.g., FIGS. 3, 4, and 5).

In operation 205, the control circuitry of a medical device can receive voice input from a vocal utterance spoken by a user of the medical device. The voice input can be indicative of a task associated with using the medical device. One example of a medical device to perform operation 205 is depicted in FIG. 1, where the infusion pump system 10 includes the control device 50 that is in communication with the portable pump device 60 of the infusion pump system 10. As explained, the control device 50 can receive the voice input via the microphone 51 located in the remote control device 50. In other embodiments, another type of control device 50 (e.g., a tablet computing device, a blood glucose meter device, a body-worn continuous glucose monitoring device, a custom remote, a removably attachable control device, and the like) can perform the same steps as the remote control device 50, which is implemented in FIG. 1 as a smartphone device. In still further embodiments, no remote control device 50 is included in the infusion pump system 10, and the receipt of the voice input can received directly at the microphone 61 housed in the portable pump device 60.

In operation 210, the voice input is coded to digital format (e.g., an "audio file," "waveform," "sample," and the like) by the control circuitry of the medical device and saved in memory of the medical device. For example, in the context of the infusion pump system 10 of FIG. 1, the remote control device 50 can convert the voice input to digital format and save the digitized voice input in memory.

In operation 215, the digitized voice input is analyzed by the control circuitry of the medical device to determine one or more candidate textual transcriptions corresponding to the voice input. This step of the process 200 can be optionally performed using an ASR system, as explained above in regard to FIG. 1. In some embodiments, the control circuitry of the medical device communicates with a remote server to perform some or all of the ASR system operations.

In operation 220, the control circuitry of the medical device compares the textual transcription(s) from operation 215 to tasks pertaining to the medical device and that are stored in a task database. In some embodiments, the task database is stored in the memory of the medical device. In alternative embodiments, the task database is stored at a remote server system that is accessible by the medical device over a network such as the internet. One or more tasks that are stored in the task database can be identified as candidates to have a correspondence to the textual transcription(s). A statistical confidence level can be generated in regard to the correspondence between the textual transcription(s) and the candidate task(s).

In operation 225, the control circuitry of the medical device compares the statistical confidence level(s) generated in operation 220 to a predetermined threshold confidence level. If one and only one particular task has a statistical confidence level that surpasses the threshold confidence level, that particular task is selected as the task to present to the user, and the process 200 moves to operation 235. However, if no particular task has a statistical confidence level that surpasses the threshold confidence level, or if multiple tasks have statistical confidence level(s) that surpass the threshold confidence level, then the process 200 moves to operation 230. In alternative embodiments, if multiple tasks have statistical confidence level(s) that surpass the threshold confidence level, then the task with the highest confidence level is selected as the task to present to the user. In some such alternative embodiments, the task with the highest confidence level is only selected if the confidence level of the task is greater than the next highest confidence level by more than a predetermined differential threshold value.

In operation 230, the control circuitry of the medical device requests user clarification in regard to the voice input that was previously provided by the user in operation 205. The request for user clarification can be presented audibly to the user by voice synthesis via the medical device, by displaying information on the user interface display of the medical device, or both. In some circumstances, the clarification requested may be in relation to a candidate task that had a statistical confidence level that was determined to be less than the threshold confidence level. For instance, such a clarification request could be, "Do you want to stop the pump?" In another circumstance, the clarification requested may be general, rather than in relation to a candidate task.

For example, in that circumstance the clarification request could be, "Your input was not understood—please try again," or another indication that the voice input should be restated. After requesting user clarification, the process 200 returns to operation 205 and waits for further voice input from the user.

In operation 235, after selecting a task in operation 225, the control circuitry of the medical device characterizes the selected task, as needed, in preparation for presentation to the user for confirmation of the task. For example, some data may need to be obtained and some calculations may need to be performed to prepare the task for presentation to the user. To provide a more specific example, as described in the context of the infusion pump system 10 of FIG. 1, the nutritional content of the food items (bagel and orange juice) were obtained from a database. The nutritional content of the bagel and orange juice were included in the task as presented to the user for confirmation.

In operation 240, the control circuitry of the medical device presents the task to the user for user confirmation. The task can be presented audibly to the user by voice synthesis via the medical device, by displaying information on the user interface display of the medical device, or both. As described in relation to the infusion pump system 10 of FIG. 1, in some embodiments the presentation of the task can include a description of the task and selectable elements on the user interface of the medical device such as buttons or soft-keys corresponding to "YES" and "NO" or the user can provide "yes" or "no" inputs by speaking to the medical device. The user's responsive input is received by the control circuitry of the medical device in operation 245.

In operation 250, the control circuitry of the medical device determines whether the user input received in operation 245 was a confirmation or a denial of the task that was presented to the user. If the user input was a denial of the task that was presented to the user, the process 200 proceeds to operation 230 where user clarification is requested as described above. If the user input was a confirmation of the task that was presented to the user, the process 200 proceeds to operation 255 where the control circuitry of the medical device communicates the task to other portions of the device so as to implement the task. In this embodiment, the control circuitry communicates the task to the pump controller to implement the task. In the context of the infusion pump system 10 of FIG. 1, the operation is exemplified in step F with the remote control device 50 sending a wireless signal 45 to the portable pump 60 to initiate a bolus of 4.9 units of insulin.

Figure 3:
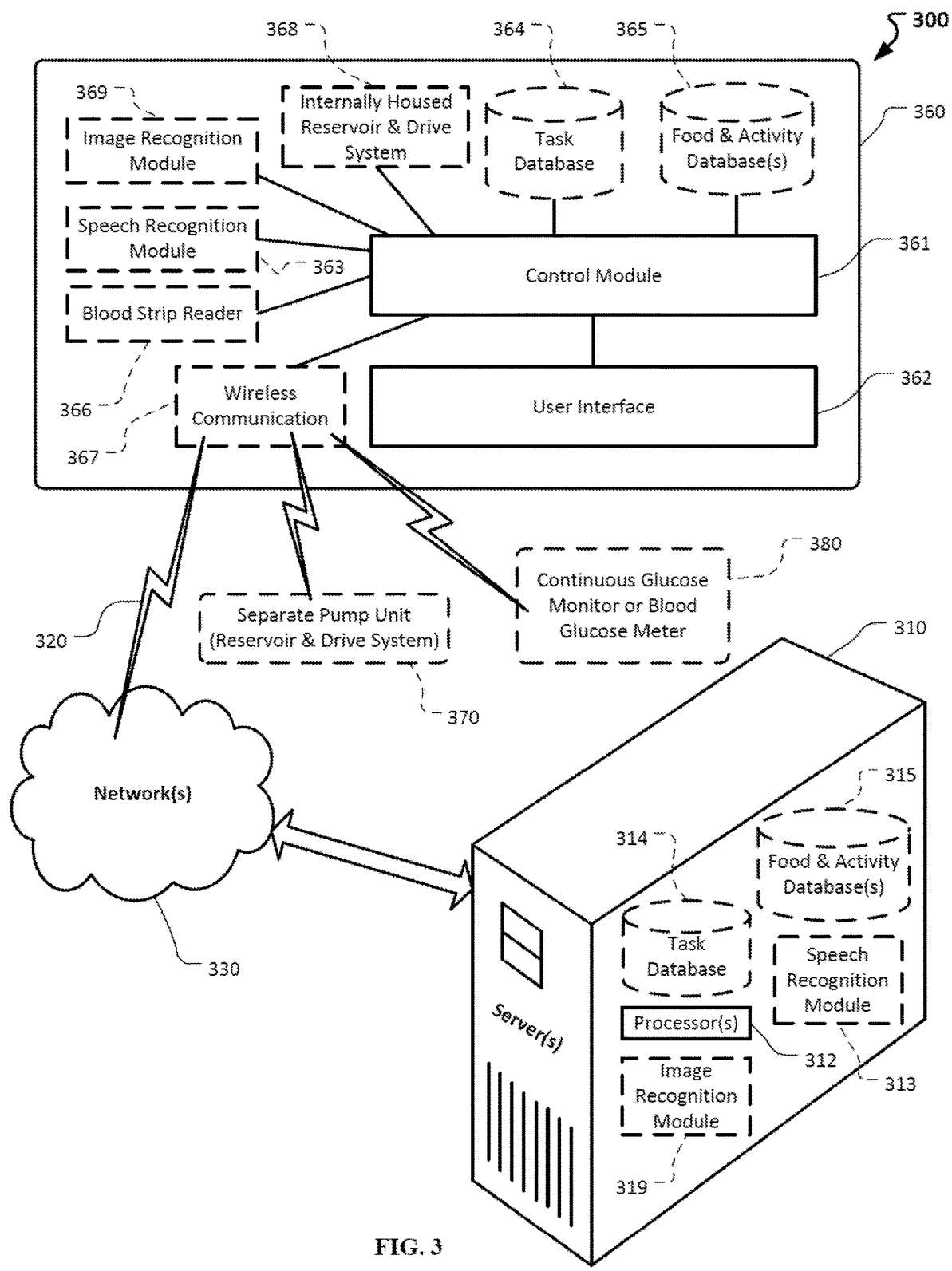
FIG. 3 is a schematic diagram of an infusion pump system including with speech recognition equipment, in accordance with some embodiments.

Now referring to FIG. 3, various embodiments of a portable infusion pump system 300 can include a pump controller device 360 that is equipped with speech recognition capabilities. As described further herein, the speech recognition process can take place at the pump controller device 360, at a remote server 310 (which can be multiple servers in a system) in communication with the pump controller device 360, or by a combination of both the pump controller device 360 and the remote server 310. Certain items of the infusion pump system 300 are shown with dashed lines to indicate that they are optional or alternative items, as explained below.

Figure 4:
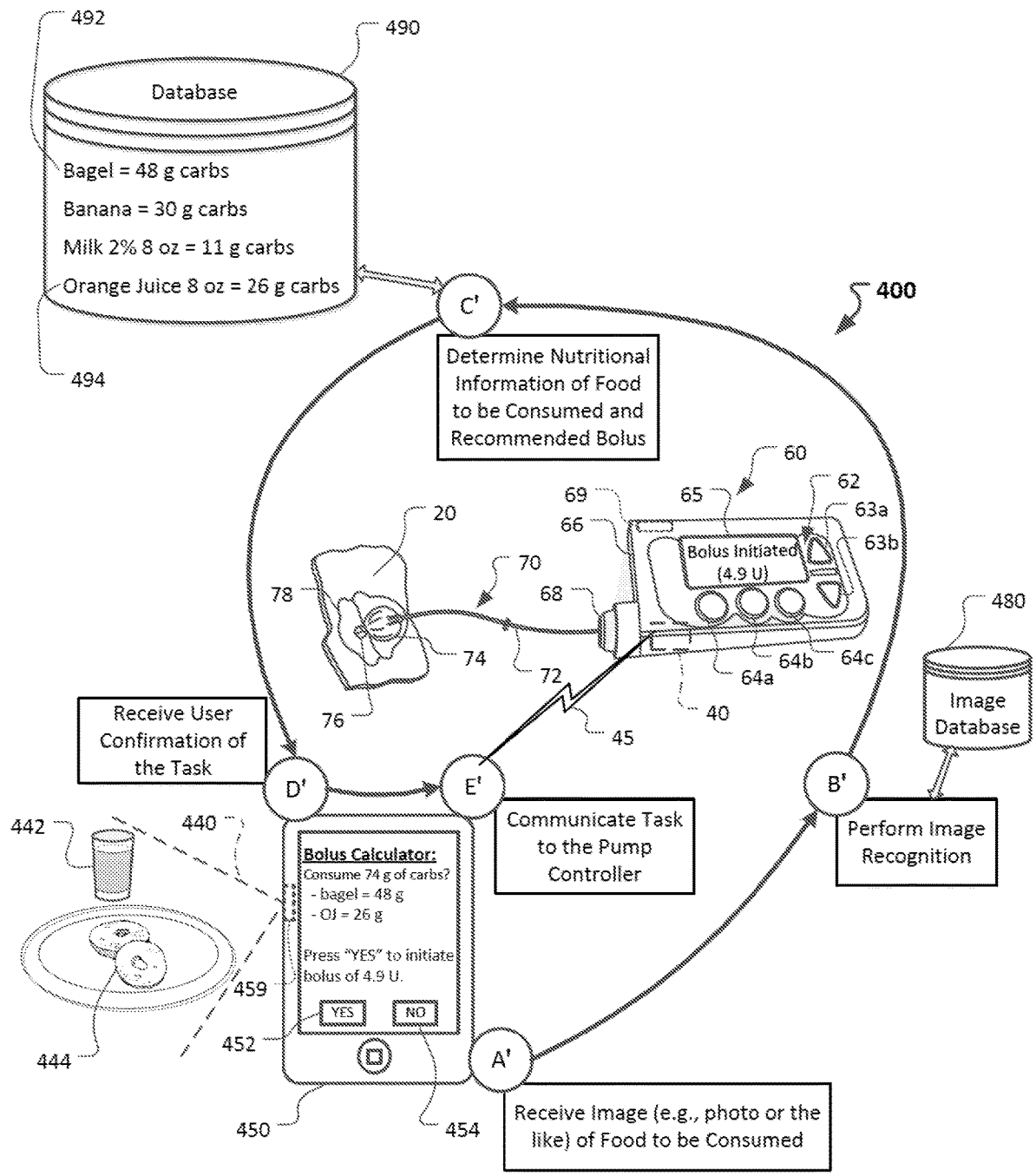
FIG. 4 is a diagram depicting the use of an infusion pump system equipped with image recognition capabilities, in accordance with some embodiments.
Figure 5:
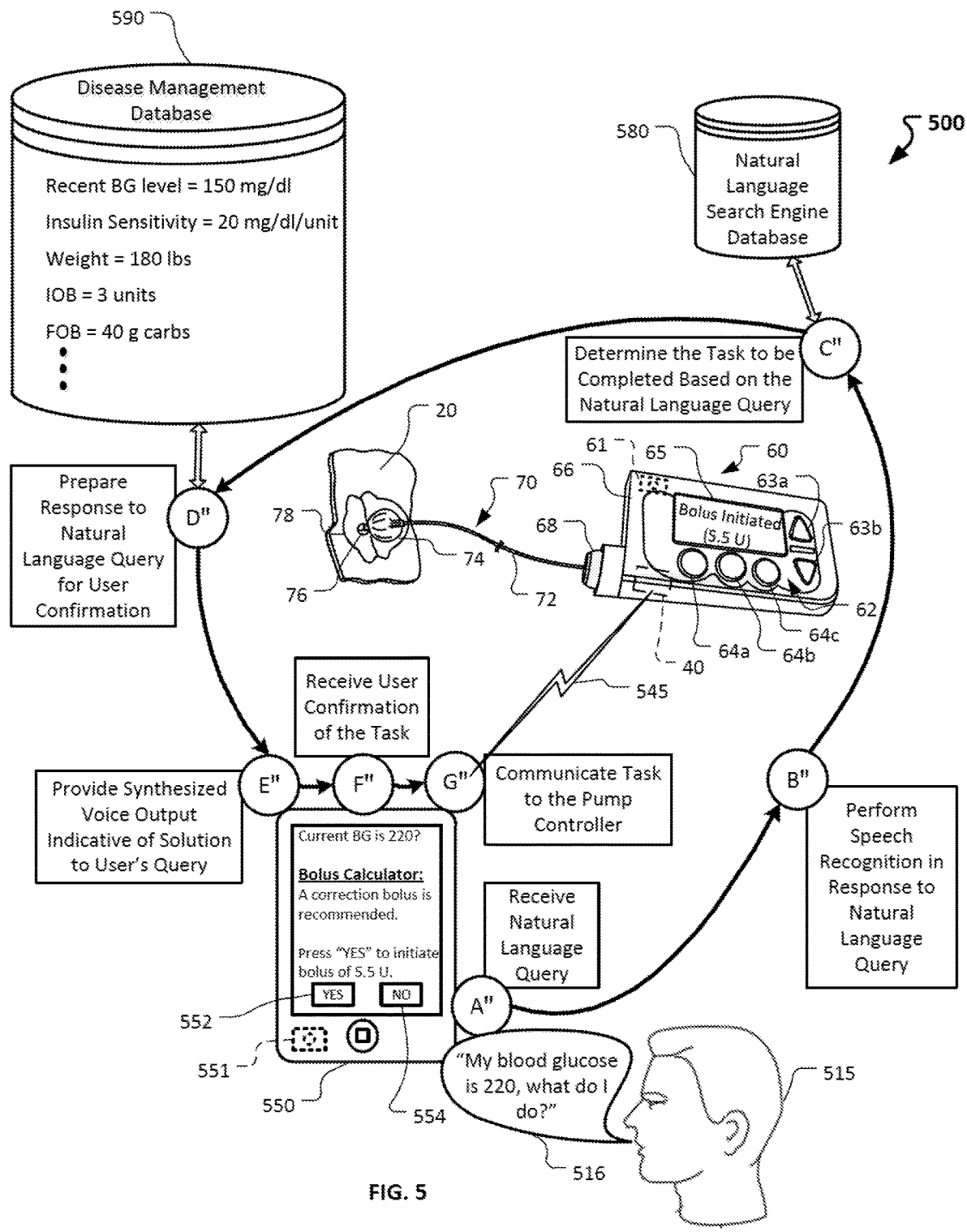
FIG. 5 is a diagram depicting the use an infusion pump system equipped with natural language speech recognition capabilities, in accordance with some embodiments.

The pump controller device 360 includes a control module 361 that can be made up of one or more components. In this embodiment, the control module 361 is configured to communicate control or power signals to the other components of the infusion pump system 300, and to receive inputs and signals therefrom. In some embodiments, the control circuitry can include a main processor board that is in communication with a power supply board. The control circuitry can include at least one processor that coordinates the electrical communication to and from the control module 361 and other components of the infusion pump system 300. For example, the user interface 362 of the pump controller device 360 can include input components (e.g., buttons, touchscreen, microphone, or a combination thereof) and output components (e.g., display screen, speaker, vibratory device, or a combination thereof) that are electrically connected to the control circuitry of the control module 361. In some embodiments, the control module 361 can receive input commands from a user's button selections (e.g., buttons as shown in FIG. 1, 4, or 5), and thereby cause the display device of the user interface 362 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge, the amount of battery life remaining, or the like).

The processor of the control module 361 can be arranged on a main processor circuit board of the control module 361 along with a number of other electrical components such as computer-readable memory devices. The control circuitry can be programmable in that the user or a clinician may provide one or more instructions to adjust a number of settings for the operation of the infusion pump system 300. Such settings may be stored in the memory devices of the control module 361. Furthermore, the control module 361 may include one or more dedicated memory devices that store executable software instructions for the processor. The control module 361 may include other components, such as sensors, that are electrically connected to the main processor board. A rechargeable battery pack (not shown) may provide electrical energy to the control module 361, and to other components of the pump controller device 360 (e.g., user interface 362, speech recognition module 363, and others).

Still referring to FIG. 3, the user interface 362 of the pump controller device 360 permits a user to monitor and control the operation of the pump controller device 360. For example, the user interface 362 can include a display device having an active area that outputs information to a user, and buttons (e.g., actuatable buttons as shown in FIG. 1, 4, or 5, or touchscreen soft-key buttons defined on the display device) that the user can use to provide input. The display device can be used to communicate a number of settings or menu options for the infusion pump system 300. The display may include an active area in which numerals, text, symbols, images, or a combination thereof can be displayed (refer, for example, to FIG. 1). For example, the user may press one or more buttons to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge, or the like). In some embodiments, the user can adjust the settings or otherwise program the control module 361 via the user interface 362. For example, in embodiments of the infusion pump system 300 configured to dispense insulin, the user may press one or more of the buttons of the user interface 362 to change the dispensation rate of insulin or to request that a bolus of insulin be dispensed immediately or at a scheduled, later time.

The user interface 362 can also include components that facilitate voice communications between the pump controller device 360 and a user. In some embodiments, the user interface 362 includes a microphone (refer, for example, to microphone 51 or microphone 61 in FIG. 1). The microphone can receive voice input from the user, such as when the user wants to initiate a task using the speech recognition capabilities of the infusion pump system 300. Further, in some embodiments, the user interface 362 includes a speaker. The speaker can be used to provide audible communications (e.g., synthesized speech, audible beeps or tones, or the like) from the infusion pump system 300 to the user. For example, the infusion pump system 10 of FIG. 1 provided an audible characterization of the task to the user 15 in step E, and the process 200 of FIG. 2 provided an audible request for clarification to the user in operation 230.

Still referring to FIG. 3, the pump controller device 360, the remote server 310, or both the pump controller device 360 and the remote server 310, can optionally include speech recognition modules 363 and 313, task databases 364 and 314, and food and activity databases 365 and 315 respectively. These subsystems can facilitate voice communications between the pump controller device 360 and a user, for example, as described in reference to FIG. 1. The pump controller device 360 and the remote server 310 can be in communication with each other via a network 330, such as a wireless network, WiFi network, wired network, LAN, intranet, internet, telephone network, and so on—and combinations of such networks. The pump controller device 360 can communicate with the network 330 using a wireless connection 320, or a wired connection, or both a wireless connection 320 and a wired connection. Such wireless communication may occur, for example, via a wireless communication module 367 using radio-frequency, Bluetooth, WiFi, or other such wireless communication methods, and combinations of such methods. The remote server 310 can include one or more processors 312 that can execute instructions embodied in a computer program. The processors 312 can include, by way of example, both general and special purpose microprocessors, and any one or more processors of any kind of digital computer.

In some embodiments of the infusion pump system 300, the pump controller device 360 includes the speech recognition module 363, task database 364, and food and activity database 365, while the remote server 310 may not have analogous sub-systems. In such embodiments, the speech recognition process and other operations for facilitating voice communications between the pump controller device 360 and a user are performed entirely at the pump controller device 360. In alternative embodiments of the infusion pump system 300, the remote server 310 includes speech recognition module 313, task database 314, and food and activity database 315, while the pump controller device 360 does not have analogous sub-systems. In such embodiments, the speech recognition process and other operations for facilitating voice communications between the pump controller device 360 and a user are performed by the remote server 310.

In particular embodiments, both the pump controller device 360 and the remote server 310 include the sub-systems for performing speech recognition and other operations for facilitating voice communications between the pump controller device 360 and a user. That is, the pump controller device 360 includes the speech recognition module 363, the task database 364, and the food and activity database 365; and in addition the remote server 310 includes the speech recognition module 313, the task database 314, and the food and activity database 315. In alternative embodiments, one or more of the sub-systems are located in both the pump controller device 360 and the remote server 310, but not all of the sub-systems are located in both.

Various techniques can be used to coordinate the activities between the pump controller device 360 and the remote server 310 when some or all of the sub-systems are arranged in both the pump controller device 360 and the remote server 310. For example, in some embodiments the processing can be initiated locally at the pump controller device 360, and if the pump controller device 360 is unable to attain the threshold statistical confidence levels for the textual transcription of the voice signal or the task matching (refer to FIG. 1), then the sub-systems of the remote server 310 can be activated to assist the pump controller device 360. If the remote server 310 attains results with higher statistical confidence levels, then the results from the remote server 310 can be used rather than the results from the pump controller device 360. That technique may be beneficial because, for example, the task database 314 and the food and activity database 315 at the remote server 310 may have a larger library of data than the task database 364 and the food and activity database 365 at the pump controller device 360. In another example, processing in the sub-systems of both the pump controller device 360 and the remote server 310 can be initiated concurrently, and whichever completes processing first can be used for presentation to the user. Or, when processing in the sub-systems of both the pump controller device 360 and the remote server 310 are initiated concurrently, the results having the highest statistical confidence level can be used for presentation to the user. It should be understood that many other arrangements for coordinating the activities between the pump controller device 360 and the remote server 310, when some or all of the sub-systems are arranged in both the pump controller device 360 and the remote server 310, are envisioned and within the scope of this disclosure.

The speech recognition modules 363 and 313 are electrical communication with the control module 361. Optionally, the speech recognition modules 363 and 313 can facilitate the operations of an ASR ("automated speech recognition") system. Using the ASR system, a digitized audio signal of a user voice input can be transcribed to one or more candidate text transcriptions that are correlated to the audio signal. In some embodiments, statistical confidence values for the candidate transcriptions are generated. In particular embodiments, the transcription with the highest confidence value may be selected as the designated transcription by the ASR system. Other ASR techniques may also be used to create transcription(s), and to select which candidate transcription to use as the designated transcription.

The task databases 364 and 314 are electrical communication with the control module 361. The task databases 364 and 314 are data repositories containing textual tasks and code that relate to the operation of the infusion pump system 300. The textual tasks contained in the task databases 364 and 314 can be compared to the textual transcriptions provided from the ASR system in operation in the speech recognition modules 363 and 313. Accordingly, candidate tasks can be identified as matches with voice inputs provided by a user of the infusion pump system 300. In some embodiments, when no matching task is determined that surpasses a statistical confidence threshold value, the infusion pump system 300 may prompt the user for clarification of the voice input.

The food and activity databases 365 and 315 are electrical communication with the control module 361. The food and activity databases 365 and 315 are data repositories containing data and other types of information that can be used to pre-process a task in preparation presentation to the user and in preparation for implementation of the task. For example, in the infusion pump system 10 of FIG. 1 the database 90 contained the nutritional information for the food items (a bagel and orange juice) that the user 15 identified in the statement 16. The nutritional information was used to populate the task that was presented to the user 15 and communicated to the portable pump 60 for execution.

Still referring to FIG. 3, optionally, the pump controller device 360 may also serve as the pump unit for the infusion pump system 300, thereby dispensing medicine from the same housing that contains the control module 361 and other components. In those particular embodiments, the pump controller device 360 can be optionally equipped with an internally housed medicine reservoir and drive system 368 in hardwired electrical communication with the control module 361. Such embodiments of the portable infusion pump system 300 can employ a reusable pump apparatus. Therefore, in those embodiments, the infusion pump system 300 may optionally serve as a reusable device that houses the control module 361 and the integral reservoir and pump drive system 368 within a single housing construct. In those circumstances, the pump controller device 360 can be adapted to slidably receive a medicine cartridge in the form of a carpule that is preloaded with insulin or another medicine, or alternatively can be adapted to have a refillable internal reservoir. The pump drive system 368 can act upon the fluid cartridge to controllably dispense medicine through an infusion set (refer, for example, to infusion set 70 in FIG. 1) and into the user's tissue or vasculature. In this embodiment, the user can wear the pump controller device 360 on the user's skin under clothing or in the user's pocket while receiving the medicine dispensed through the infusion set.

Still referring to FIG. 3, as an alternative to the internally housed medicine reservoir and drive system 368, the infusion pump system 300 can include a separate pump device 370 (including a reservoir and a drive system) that is in communication (wireless communication or a releasable electrical connection) with the pump controller device 360. In these embodiments, the separate pump device 370 can be configured as a disposable and non-reusable pump component while the controller device 360 is configured to be reused with a series of the pump devices 370. In the depicted embodiment shown in FIG. 3, wireless communications are used between the separate pump device 370 and the pump controller device 360, using the wireless communication module 367 in the pump controller device 360. The wireless communications of the wireless communication module 367 can utilize any of a variety of wireless communication technologies. For example the wireless communication module 367 can employ NFC (near field communication), Bluetooth, RF (radio frequency), infrared, ultrasonic, electromagnetic induction, and the like, and combinations thereof. Alternatively, a releasable electrical connection can be used between the separate pump device 370 and the pump controller device 360 so as to provide hardwired electrical communication between the control module 361 of the controller device 360 and the drive system of the pump device 370. In such embodiments, the separate pump device 370 can be removably attachable with the controller device 360 so that the two housings are mechanically mounted together during dispensation of the medicine from the separate pump device 370.

In brief, in embodiments of the infusion pump system 300 that include the separate pump device 370, the pump controller device 360 may be configured as a reusable component that provides electronics and a user interface to control the operation of the infusion pump system 300, and the separate pump device 370 can be a disposable component that is discarded after a single use. For example, the separate pump device 370 can be a "one time use" component that is thrown away after the fluid cartridge therein is exhausted. Thereafter, the user can wirelessly connect or removably mount a new separate pump device 370 to the reusable pump controller device 360 for the dispensation of a new supply of medicine from the new pump device 370. Accordingly, the user is permitted to reuse the pump controller device 360 (which may include complex or valuable electronics) while disposing of the relatively low-cost separate pump device 370 after each use. Such an infusion pump system 300 can provide enhanced user safety as a new separate pump device 370 is employed with each new fluid cartridge.

Still referring to FIG. 3, the pump controller device 360 can also optionally include an internal blood strip reader 366 mounted therein and being in electrical communication with the control module 361. In such embodiments of the pump controller device 360, test strips (e.g., blood test strips) containing a sample of the user's blood can be inserted into the blood strip reader 366 portion of the pump controller device 360, to be tested for characteristics of the user's blood. The results of the analysis can be used to affect the dosage or schedule of medicine dispensations from the pump controller device 360 to the user as determined by the control module 361. As an alternative to or in addition to the internal blood strip reader 366 housed in the pump controller device 360, the pump controller device 360 can be configured to communicate with an external blood glucose detection device 380, such as a continuous glucose monitor or a handheld blood glucose meter. For example, the test strips (e.g., glucose test strips) containing a sample of the user's blood can be inserted into external handheld blood glucose meter 380, which then analyzes the characteristics of the user's blood and communicates the information (via a wired or wireless connection) to the pump controller device 360. In other embodiments, the user interface 362 of the pump controller device 360 can be employed by the user to manually enter the user's blood glucose information as reported on a screen of a handheld blood glucose meter 380. In still other embodiments, the infusion pump system 300 can include a continuous glucose monitor 380 (as an alternative to or in addition to the internally housed blood strip reader 366) that can continuously monitor characteristics of the user's blood and communicate the information (via a wired or wireless connection) to the pump controller device 360.

Optionally, as shown in FIG. 3, the pump controller device 360 can also optionally include an image recognition module 369. As described in more detail below (e.g., in connection with FIG. 4), the image recognition module 369 can be used as part of an image recognition operation that facilitates efficient communications between the user and the pump controller device 360. The image recognition module can include a digital camera, image storage memory, and one or more programs configured to determine candidate matching images from a user-input image (as described in detail below). In optional embodiments, both the pump controller device 360 and the remote server 310 include the subsystems for performing image recognition and other operations for facilitating efficient communications between the pump controller device 360 and a user. That is, the pump controller device 360 includes the image recognition module 369, and in addition the remote server 310 includes the image recognition module 319.

Referring now to FIG. 4, some embodiments of an infusion pump system 400 can include image recognition equipment for purposes of receiving and responding to a user's digital image input. The infusion pump system 400 may include, among other elements, a control device 450 and the pump device 60 that receives communications from the control device 450. Similar to the embodiment previously described in connection in FIG. 1, the control device 450 wirelessly communicates with the pump device 60, but the system 400 can be implemented using a control device that is removably attached to a corresponding pump device (e.g., for hard-wired electrical communication) or using a control device that is housed together with the pump device (e.g., in a single portable construct). Optionally, the controller device 450 can be implemented as the same controller device 50 previously described in connection in FIG. 1.

In this example, the infusion pump system 400 can be configured to perform a series of steps A' through E' are illustrated that describe operations of an example infusion pump system 400 including with image recognition equipment. By incorporating image recognition capabilities within the infusion pump system 400, user communications with a portable pump 60 can be enhanced and simplified. As a result, the accuracy and completeness of the data entered by the user into the portable pump 60 can be improved, and the user can experience greater convenience and time efficiency. In some embodiments of the infusion pump system 400, speech recognition capabilities (e.g., as described in reference to FIG. 1) can be included along with the image recognition capabilities.

As previously described, the infusion pump system 400 can include the remote control device 450 in electrical communication with the portable pump 60, which is used to supply insulin or another medication to a user via an infusion set 70 attached to and penetrating the user's skin 20. In some embodiments, the portable pump 60 includes the user interface 62 comprised of input devices such as buttons 63a, 63b, 64a, 64b, 64c and output devices such as display 65. In addition, in this embodiment the user can communicate with the infusion pump system 400 by providing image input, such as example digital image 440 of a bagel 444 and a serving of orange juice 442. In particular embodiments, the portable pump 60 may also include the wireless communications circuit 40 that facilitates short-range wireless communications 45 between the internal control circuitry of the portable pump 60 and the external remote control device 450. As with the previously described system 10 of FIG. 1, the infusion pump system 400 is configured to controllably dispense a medicine to be infused into the tissue or vasculature of a targeted individual, such as a human or animal patient.

Still referring to FIG. 4, in this example at step A', the remote control device 450 is used to take a photographic image 440 (e.g., a digital photo) of a bagel 444 and a serving of orange juice 442 that the user is going to consume. As will be described further, the infusion pump system 400 will receive and process the image 440 and recommend a bolus dispensation of insulin to compensate for the bagel 444 and orange juice 442 to be consumed by the user. In some embodiments, a reference object of known size is optionally included in the photographic image 440 to assist with estimating the quantity of food items in the image 440. Examples of such reference objects include the user's hand or finger, a business card, a coin, an insulin pump, and the like.

In this embodiment, the image 440 is received by a digital camera system 459 housed in the remote control device 450. The remote control device 450 includes electronic circuitry for digitizing the image 440 into pixels. The digitized image can be stored (permanently or temporarily) in a computer-readable memory device of the remote control device 450. In other embodiments, the image 440 can be received by a digital camera system 69 housed in the pump device 60, and the image can be stored in a computer-readable memory device of the remote control device 50.

In this embodiment the control device 450 is depicted as a smart phone device, but it should be understood from the description herein that, in other embodiments, the control device 450 can be implemented in the form of devices other than a smart phone device. Some other example devices that can be used similarly to the remote control device 450 can include, but are not limited to, a personal computer, a tablet computing device, a blood glucose meter device (e.g., an external blood strip reader), a continuous glucose meter device, a wearable computing device (e.g., glasses equipped with a camera and computer network connectivity), a PDA, a digital camera, or a custom remote device. In still other embodiments, the control device is not a remote device, but instead is included as part of, or mechanically attached together with, the pump device. For instance, in such embodiments the pump device of the infusion pump system can be equipped with the capabilities to perform the functions described herein in regard to the remote control device 450. Further, in some embodiments certain operations or parts of certain operations may be performed at a remote server system, including a cloud-based server system, rather than completely on a personal computing device such as the remote control device 450. Accordingly, the remote control device 450, or equivalent, can be connected to a network such as the internet or an intranet system. Such a division of tasks may provide better process optimization, computational efficiency, and response time.

Still referring to FIG. 4, in this example at step B', image recognition is performed in response to receiving the digital file of image 440. For example, in response to the receipt of the image 440, the control device 450 can perform an image recognition function so as to determine that the food items depicted in the image 440 include a bagel and a glass of orange juice. In one implementation, the digital file of image 440 is matched to one or more candidate images (e.g., model images of food items or other items) from an image database 480. The image database 480 can be stored in a computer-readable memory device of the remote control device 450, stored in a computer-readable memory device of the portable pump 60, stored in a computer-readable memory device of a remote server system in communication with the remote control device 450, or a combination thereof. The image recognition process can be performed at the remote control device 450 or portable pump 60, at the remote server, or at both the remote control device 450 or portable pump 60 and the remote server. Performing the image recognition at a remote server may provide better process optimization, computational efficiency, and response time due to the high level of data processing power required for efficient image recognition—but it is not a requirement to perform the image recognition at a remote server.

In this embodiment, the control device 450 is equipped with an image recognition module (refer, for example, to element 369 in FIG. 3) that is configured to compare the digital file of image 440 with digital files of images that are stored in the image database 480. This process can result in finding candidate matching images. Each image is composed of pixels that are expressed as a series of numbers. One approach to matching the images to use the image recognition module to search for patterns and sequences in numerical data that make up the digital files. If the image recognition module can identify similar numerical series in multiple images, it can recognize that the images may be all of the same subject. In some embodiments, a statistical confidence level can be calculated in regard to the candidate matching images. In particular embodiments, the image with the highest confidence value may be selected by the image recognition system as the designated matching image. Other techniques may also be used to select which candidate image to use as the designated matching image. For example, in some embodiments statistical priority can be given to foods that the user has previously utilized the image recognition technique to identify. In some circumstances, no candidate image having a confidence value that surpasses a threshold confidence level is identified. In some such circumstances, the remote control device 450 may request clarification from the user, or may request more information from the user (such as another photograph from a different perspective or using different lighting). Such requests may be presented to the user audibly using voice synthesis at the remote control device 450, or visually by presenting an indication on the display of the remote control device 450, or by a combination of audible and visual indicators.

Still referring to FIG. 4, in this example at step C', nutritional information of the food in the image 440 is obtained from database 490, and a recommended bolus dispensation is calculated. In some embodiments, the calculation of the recommended bolus dispensation can take into account the user's preferred dispensation method, such as a fast bolus, a timed bolus (with preferred time of delivery), or a combination bolus (including a preferred division between a present and an upcoming timed dispensation, and the preferred duration of the upcoming timed dispensation). The database 490, as with the image database 480, can be stored in one or more computer-readable memory devices at various locations including at the remote control device 450, the portable pump 60, a remote server system including cloud-based servers, or at a combination of such locations. As depicted by this example, the database 490 can contain nutritional information for a variety of food items. The nutritional information can include, but is not limited to, carbohydrates, fat, protein, and the glycemic index for food items. In some embodiments, the database 490 can also include the user's most current blood glucose reading, an insulin-on-board level, an insulin sensitivity factor for the user, and the like. In particular embodiments, some or all of such nutritional information and other data can be considered when the task is being prepared for presentation to the user. For example, in response to the receipt of the image 440, the bagel's nutritional information 492 and orange juice's nutritional information 494 can be queried from the database 490. In some embodiments, the data stored in database 490 is customizable by the user as described above in regard to database 90 of FIG. 1. The user's custom nutritional information can be given preference in the database 490 over the default nutritional information. In some embodiments, as part of the preparation for presenting the task to the user, the user may first be presented with a request for additional information. For example, the user may be presented with a request to input a current blood glucose level. After the receipt of such addition information, the preparation for presenting the task to the user can be completed.

In some embodiments, step C' can be performed as follows. The candidate matching images selected from the image database 480 as determined by the image recognition process of step B' can have metadata associated therewith. The metadata can identify the type of food in the image(s) (e.g., a bagel and a serving of orange juice). Using such metadata, the nutritional information for the food types can be queried from the database 490. The nutritional information obtained from the database 490 can be used in computations—along with other parameters such as the user's most current blood glucose reading, an insulin-on-board level, an insulin sensitivity factor for the user, and the like—to determine a recommended bolus dispensation. The descriptions of the food items identified as matching the image 440, and the recommended associated bolus can then be characterized in preparation for presentation to the user (for subsequent user confirmation).

Still referring to FIG. 4, in this example at step D', the task is presented to the user for confirmation that the task is what the user 15 desires. The task may be presented to the user audibly using voice synthesis at the remote control device 450, or visually by presenting an indication on the display of the remote control device 450, or by a combination of audible and visual indicators. For example, in response to the image 440, the user is presented with information indicating that the infusion pump system 400 has identified a task related to the user's intent to consume 74 grams of carbohydrates (48 grams from the bagel and 26 grams from the orange juice), and that the infusion pump system 400 recommends a corresponding bolus dispensation of 4.9 Units of insulin. To confirm that task, the user can select "YES" 452 on the remote control device 450. In response to a selection of the "YES" button 452, the control device 450 can communicate with the pump device 60 so as to initiate the dispensation of the bolus dosage (e.g., 4.9 Units in this example), as described below. Or to deny that task, the user can select "NO" 454 on the remote control device 450. Optionally, in response to a selection of the "NO" button 454, the control device 450 can present the user with an option to manually input or verbally speak a specific number for a bolus dosage that is different from the suggested dosage displayed on the screen at step E. Alternatively, or in addition to, the manual selection of "YES" 452 or "NO" 454, the user may speak "yes" or "no" to the remote control device 450 to confirm or deny the task presented.

In this example at step E', the remote control device 450 communicates the task to the portable pump 60 for activation of the portable pump 60 in accordance with the task confirmed by the user (e.g., after the user selected the "YES" button 452). In the example, the display 65 of the portable pump 60 indicates that a bolus dispensation of 4.9 Units has been initiated. In this embodiment, communications between the remote control device 450 and the portable pump 60 are conducted by short-range wireless technologies such as, but not limited to, RF, Bluetooth, NFC, IR, and the like. Accordingly, the portable pump 60 can include a wireless communication circuit 40 that sends and receives data in cooperation with the remote control device 450. In alternative embodiments, the communications between the remote control device 450 and the portable pump 60 can be via a hardwired connection therebetween.

In another embodiment, rather than (or in addition to) using photographic image recognition to ascertain nutritional information for food to be consumed, a portable spectroscope scanner system can be used to ascertain nutritional information for food to be consumed. In this technique, a user can scan food items to be consumed using a portable spectroscope scanner. The spectroscope scanner will create a spectrograph of the food items that can be analyzed to determine nutritional information of the food items. Some spectroscope scanner systems may utilize a reference material placed next to the food for calibration as part of routine use or occasionally.

In some embodiments, the spectroscope scanner transmits the spectrograph data to another processing device that operates a spectrograph analysis application that can be run to determine the nutritional information of the food that was scanned. Such processing devices can include a cloud-based computer system or a local computing device, such as a smartphone, tablet PC, desktop PC, an infusion pump, and the like. In some embodiments, the spectroscope scanner may be able to determine the nutritional information of the food that was scanned without the assistance of another processing device. In particular embodiments, as part of the analysis of the spectrograph, statistical priority can be given to foods that the user has previously utilized the spectrograph analysis technique to identify. The processing device that analyzes the spectrograph can determine the nutritional information and then transmit the nutritional information to the remote control device 450. The remote control device 450 can display the nutritional information to the user, and display a prompt by which the user can initiate a corresponding bolus dispensation via the portable pump device 60, in a manner analogous to that described above.

Referring now to FIG. 5, some embodiments of an infusion pump system 500 can include natural language processing ("NLP") capabilities for purposes of receiving and responding to a user's voice input. The infusion pump system 500 may include, among other elements, a control device 550 and the pump device 60 that receives communications from the control device 550. Similar to the embodiment previously described in connection in FIG. 1, the control device 550 wirelessly communicates with the pump device 60, but the system 500 can be implemented using a control device that is removably attached to a corresponding pump device (e.g., for hard-wired electrical communication) or using a control device that is housed together with the pump device (e.g., in a single portable construct). Optionally, the controller device 550 can be implemented as the same controller device 50 previously described in connection in FIG. 1.

In this example, the infusion pump system 400 can be configured to perform a series of steps A" through G" are illustrated that describe operations of an example infusion pump system 500 equipped with natural language processing ("NLP") technology. Using NLP, the infusion pump system 500 is capable of receiving instructions from a user 515 via natural language input. One or more NLP algorithms can be stored in the computer-readable memory device in as part of a speech recognition module (refer, for example, to module 363 in FIG. 3), including machine learning algorithms for language processing. By incorporating NLP capabilities within the infusion pump system 500, user communications with a portable pump 60 can be enhanced and simplified. As a result, the accuracy and completeness of the data entered by the user 515 into the portable pump 60 can be improved, and the user 515 can experience greater convenience and time efficiency.

Similar to previously described embodiments, the infusion pump system 500 can include the remote control device 550 in electrical communication with the portable pump 60 that is used to supply insulin or another medication to a user 515 via an infusion set 70 attached to and penetrating the user's skin 20. In particular embodiments, the portable pump 60 may also include the wireless communications circuit 40 that facilitates short-range wireless communications 545 between the internal control circuitry of the portable pump 60 and the external remote control device 550.

As an alternative to, or in conjunction with, pressing one or more buttons 63a, 63b, 64a, 64b, and 64c of the user interface 62 to communicate with the infusion pump system 500, the example infusion pump system 500 can receive natural language voice input from the user 515. The use of NLP technology provides an additional functionality that can enhance and simplify user 515 interactions with the portable pump 60. For instance, using natural language equipment (which may optionally a microphone 551 or 61 and a corresponding NLP software program implemented by the system 500), the need for user activation of multiple buttons 63a, 63b, 64a, 64b, and 64c for shuffling through menus may be eliminated or otherwise reduced in some circumstances. In addition, using NLP equipment, the capabilities of the infusion pump system 500 can extend beyond those that are accessible via the user interface 62. In one such example, as depicted in FIG. 5, the user 515 of infusion pump system 500 has ascertained that his or her blood glucose level is above normal at 220 mg/dl. As such, the user is concerned and desires to initiate appropriate measures to cause his or her blood glucose to reduce to a normal level.

Still referring to FIG. 4, in this example at step A", the user 515 speaks a natural language statement 516 that reflects a question or concern that the user 15 wants the infusion pump system 10 to respond to. In this example, the user 515 speaks the statement 516, "My blood glucose is 220, what do I do?" As will be described further, the infusion pump system 500 will receive and process the statement 516 and recommend a bolus dispensation of insulin to correct the user's 515 high blood glucose level.

In this example, the user 515 has made a statement 516 that identifies the user's 515 blood glucose level, but many other types of statements corresponding to other tasks, questions, or concerns can be similarly initiated using natural language voice input. For instance, in other non-limiting examples such statements can include "I am going for a 45 minute jog," "tell me about my last bolus," "how long have I been wearing this infusion set," "what do I do about the current alarm," or "how much insulin is left in my reservoir?" It should be recognized from the description herein that the user 515 can provide a wide variety of types of statements to initiate a wide variety of responses by the infusion pump system 500, and that the examples provided here are merely illustrative.

The natural language statement 516 is received by the microphone 551 of the control device 550. The remote control device 550 can include electronic circuitry for converting the statement 516 to an audio signal (e.g., an "audio file," "waveform," or "sample") that corresponds to the statement 516. The audio signal corresponding to the statement 516 can be saved in the memory of the remote control device 550. In other embodiments, the natural language statement can be received by the microphone 61 housed in the pump device 60.

In this embodiment the control device 550 is depicted as a smart phone device, but it should be understood from the description herein that, in other embodiments, the control device 550 can be implemented in the form of devices other than a smart phone device. Some other example devices that can be used similarly to the remote control device 550 can include, but are not limited to, a personal computer, a tablet computing device, a blood glucose meter device (e.g., an external blood strip reader), a continuous glucose meter device, a wearable computing device, a PDA, or a custom remote device. In still other embodiments, the control device is not a remote device, but instead is included as part of, or mechanically attached together with, the pump device. For instance, in such embodiments the pump device of the infusion pump system can be equipped with the capabilities to perform the functions described herein in regard to the remote control device 550. Further, in some embodiments certain NLP operations or parts of certain NLP operations may be performed at a remote server system, including a cloud-based server system, rather than completely on a personal computing device such as the remote control device 550. Accordingly, the remote control device 550, or equivalent, can be connected to a network such as the internet or an intranet system. Such a division of tasks may provide better process optimization, computational efficiency, and response time.

Still referring to FIG. 4, in this example at step B", speech recognition is performed in response to receiving the voice input. This step is performed as described in step B of FIG. 1. A text transcription of the statement 516 is generated and stored (temporarily or permanently) in the computer-readable memory device of the control device 550, of the pump device 60, of the remote server system, or a combination thereof.

In this example at step C", the text transcription(s) of the speech recognition process from step B" is processed using a NLP program executed by the control device 550, the pump device 60, the remote server system, or a combination thereof to determine the likely meaning of the statement 516 and how the infusion pump system 500 should respond. In some cases, in addition to processing the text transcription(s) using NLP, the text transcription(s) is compared to a compilation of tasks or queries in a natural language search engine database 580 to determine the task most likely represented by the statement 516. In some embodiments, the natural language search engine database 580 is stored in the computer-readable memory device of the remote control device 550. However, the natural language search engine database 580 can also be stored in the computer-readable memory device in the portable pump 60, stored in the computer-readable memory device of a remote server system in communication with the remote control device 550 or the portable pump 60, or stored in computer-readable memory devices at a combination of such locations. In this embodiment, the natural language search engine database 580 is a storage repository that is programmed to contain an extensive number of tasks and queries that correspond to a variety of types of user voice input statements, such as statement 516. The transcription(s) of the voice input from step B" can be compared to the tasks stored in the natural language search engine database 580 to find matching tasks or queries. In some embodiments, a confidence level for the match between the transcription(s) and the task(s) or queries can be determined. The task or query with the highest confidence level can be selected. In particular embodiments, if no task query has such a confidence level that surpasses a threshold level, or if multiple tasks or queries have confidence levels that are within a differentiation threshold level of each other, the user 515 is presented with a request for clarification or more information as described above. In some such cases, the user 515 may be presented with the task or query having the highest confidence level and the user 515 may be asked whether that task is what the user 515 wants the infusion pump system 500 to perform.

Still referring to FIG. 4, in this example at step D", a response to the selected task or query from step C" is characterized in preparation for presentation to the user 515 (e.g., for subsequent user confirmation). Depending on the task or query, additional information may be acquired from a disease management database 590 as a part of the preparation step. The disease management database 590, as with the natural language search engine database 580, can be stored in one or more computer-readable memory devices at various locations including at the remote control device 550, the portable pump 60, a remote server including cloud-based servers, and at a combination of such locations. As depicted by this example, the disease management database 590 can contain types of data that are related to the user's 515 health and metabolic status. The data can include, but is not limited to, blood glucose level, insulin sensitivity, weight, insulin on board ("IOB"), and food on board ("FOB"). In some embodiments, the disease management database 590 can also include the user's 515 most current blood glucose reading, an insulin-on-board level, an insulin sensitivity factor for the user 515, and the like. In particular embodiments, some or all of such information and other data can be considered when the task or query is being prepared for presentation to the user 515. For example, in response to the statement 516, the insulin sensitivity, weight, IOB and FOB can be queried from the disease management database 590. In some embodiments, the data stored in disease management database 590 is customizable by the user 515. For example, the user 515 may input a particular insulin sensitivity factor that reflects the user's 515 insulin sensitivity. The user's 515 custom data can be given preference in the disease management database 590 over the default data. In some embodiments, as part of the preparation for presenting the task to the user 515, the user 515 may first be presented with a request for additional information. For example, the user 515 may be presented with a request to input nutritional information of food items consumed in the past few hours. After the receipt of such addition information, the preparation for presenting the task to the user 515 can be completed.

In this example at step E", the task or query is presented to the user 515 for confirmation that the task or query is what the user 515 desires. The task or query may be presented to the user 515 audibly using voice synthesis at the remote control device 550, or visually by presenting an indication on the display of the remote control device 550, or by a combination of audible and visual indicators. For example, in response to the statement 516, the user 515 is presented with information indicating that the infusion pump system 500 recommends a correction bolus dispensation of 5.5 Units of insulin. To confirm that task, the user 515 can select "YES" 552 on the remote control device 550. In response to a selection of the "YES" button 552, the control device 550 can communicate with the pump device 60 so as to initiate the dispensation of the bolus dosage (e.g., 4.9 Units in this example), as described below. Or to deny that task, the user 515 can select "NO" 554 on the remote control device 550. Optionally, in response to a selection of the "NO" button 554, the control device 550 can present the user with an option to manually input or verbally speak a specific number for a bolus dosage that is different from the suggested dosage displayed on the screen at step E. Alternatively, or in addition to, the manual selection of "YES" 552 or "NO" 554, the user 515 may speak "yes" or "no" to the remote control device 550 to confirm or deny the task presented. At step F", the remote control device 550 receives such user confirmation.

At step G", the remote control device 550 communicates the task to the portable pump 60 for activation of the portable pump 60 in accordance with the task confirmed by the user 515 (e.g., after the user selected the "YES" button 552). In the example, the display 65 of the portable pump 60 indicates that a bolus dispensation of 5.5 Units has been initiated. In this embodiment, communications between the remote control device 550 and the portable pump 60 are conducted by short-range wireless technologies such as, but not limited to, RF, Bluetooth, NFC, IR, and the like. Accordingly, the portable pump 60 can include a wireless communication circuit 40 that sends and receives data in cooperation with the remote control device 550. In alternative embodiments, the communications between the remote control device 550 and the portable pump 60 can be via a hardwired connection therebetween.

A number of embodiments of the invention have been described. Nevertheless, it will be understood that various modifications may be made without departing from the spirit and scope of the invention. Accordingly, other embodiments are within the scope of the following claims.

What is claimed is:

1. A medical infusion pump system, comprising:
    a portable housing defining a space to receive a medicine;
    a pump drive system to dispense the medicine from the portable housing when the medicine is received in the space;
    control circuitry that communicates control signals to the pump drive system to control dispensation of the medicine from the portable housing when the medicine is received in the space; and
    one or more computing devices comprising a speech recognition system, the one or more computing devices being in communication with the control circuitry, the one or more computing devices including a microphone and being adapted to communicate with the control circuitry, the one or more computing devices being adapted to receive a voice input from a user comprising an instruction to deliver a bolus and a user estimate of an amount of carbohydrates for one or more food items that have been or will be consumed by the user, the one or more computing devices being adapted to:
    1) determine a suggested bolus dosage that corresponds to the one or more food items based on at least the user estimate of the amount of carbohydrates;
    2) prompt the user to confirm or deny the suggested bolus dosage through manual interaction with a touchscreen or one or more buttons of the one or more computing devices; and
    3) communicate the confirmed suggested bolus dosage to the control circuitry once said bolus dosage is confirmed by the user,
    wherein the one or more computing devices are further configured to analyze the received voice input from the user to determine at least one textual transcript corresponding to the voice input and identify, using the at least one textual transcript, a numerical value of the amount of carbohydrates for the one or more food items that have been or will be consumed by the user, wherein the numerical value of the amount of carbohydrates for the one or more food items that have been or will be consumed by the user is used to determine the suggested bolus dosage.

2. The medical infusion pump system of claim 1, wherein the one or more computing devices comprises a remote server system, and the control circuitry is configured to communicate with the remote server system to receive user voice inputs received by the speech recognition system.

3. The medical infusion pump system of claim 1, wherein at least a portion of the one or more computing devices is disposed in the portable housing.

4. The medical infusion pump system of claim 1, wherein the one or more computing devices are further configured to display the suggested bolus dosage and at least one of (i) a food item indicated by the voice input, and (ii) a numerical value of the user estimate of the amount of carbohydrates, wherein the suggested bolus dosage and the at least one of (i) the food item indicated by the voice input, and (ii) the numerical value of the user estimate of the amount of carbohydrates are displayed simultaneously as part of a single user interface display.

5. The medical infusion pump system of claim 1, wherein information about a recent blood glucose level, insulin sensitivity, insulin-on-board, and food-on-board for the user are used to determine the suggested bolus dosage in addition to the user estimate of the amount of carbohydrates.

6. The medical infusion pump system of claim 1, wherein the one or more computing devices are further configured to, in response to the user denying the suggested bolus dosage, present the user with an option to manually input or verbally speak a specific number of units for a bolus dosage.

7. The medical infusion pump system of claim 1, wherein the one or more computing devices are further configured to present the user with an option to manually input or verbally speak a specific number of units for a bolus dosage.

8. The medical infusion pump system of claim 1, wherein the voice input comprises a specific name or type of food that the user will consume.

9. The medical infusion pump system of claim 1, wherein the one or more computing devices comprises a smartphone.

10. The medical infusion pump system of claim 9, wherein the smartphone is configured to permit the user to adjust the suggested bolus dosage.

11. The medical infusion pump system of claim 9, wherein the smartphone stores information about a recent blood glucose level, an insulin sensitivity, weight, an insulin-on-board, and a food-on-board for the user and uses this information to determine the suggested bolus dosage.

12. The medical infusion pump system of claim 1, wherein the one or more computing devices are further configured to:
    receive user input comprising a digital image that is indicative of the one or more food items consumed or to be consumed by the user of the portable infusion pump system; and
    determine another suggested bolus dosage based on the digital image.

13. The medical infusion pump system of claim 1, wherein the one or more computing devices are further configured to:
    receive user input comprising a digital image of the one or more food items consumed or to be consumed by the user of the portable infusion pump system;
    identify the one or more food items depicted in the digital image; and
    determine another suggested bolus dosage based on the identified one or more food items depicted in the digital image.

14. A method of controlling a portable infusion pump system, comprising:
    receiving a user's voice input that is indicative of a task associated with using a portable infusion pump system, wherein the voice input comprises a user estimate of an amount of carbohydrates that has been or will be consumed by the user and an instruction to deliver a bolus;

determining a suggested bolus dosage using at least the user estimate of the amount of carbohydrates;

in response to receiving the voice input, displaying, on a display screen, the suggested bolus dosage;

prompting a user to confirm or deny the suggested bolus dosage through manual interaction with a touchscreen or one or more buttons of a user interface, wherein if the user denies the suggested bolus dosage, the user is presented with an option to manually input or verbally speak a specific number of units for a bolus dosage;

communicating said bolus dosage to control circuitry in the portable infusion pump system in response to confirmation of the suggested bolus dosage by the user;

analyzing the received voice input to determine at least one textual transcript corresponding to the voice input; and identifying, using the at least one textual transcript, a numerical value of the amount of carbohydrates that have been or will be consumed by the user, wherein the numerical value of the amount of carbohydrates that have been or will be consumed by the user is used to determine the suggested bolus dosage.

15. The method of claim 14, wherein the display screen comprises the touchscreen.

16. The method claim 14, further comprising:
receiving user input comprising a digital image that is indicative of a food item consumed or to be consumed by the user of the portable infusion pump system; and
controlling the portable infusion pump system to change an operation of the portable infusion pump system based upon the user input comprising the digital image.

17. The method of claim 16, further comprising prompting the user via the user interface to confirm the operation change of the portable infusion pump system in response to receiving the user input comprising the digital image.

18. The method of claim 17, wherein the operation change comprises calculating or initiating a bolus dispensation of a medicine from the portable infusion pump system.

19. The method of claim 14 further comprising, displaying, on the display screen and along with the suggested bolus dosage, at least one of (i) a food item indicated by the voice input, and (ii) a numerical value of the user estimate of the amount of carbohydrates, wherein the suggested bolus dosage and the at least one of (i) the food item indicated by the voice input, and (ii) the numerical value of the user estimate of the amount of carbohydrates are displayed simultaneously as part of a single user interface display.

20. The method of claim 14, wherein information about a recent blood glucose level, insulin sensitivity, insulin-on-board, and food-on-board for the user are used to determine the suggested bolus dosage in addition to the user estimate of the amount of carbohydrates.

* * * * *